US010913718B2

(12) United States Patent
Eddaoudi et al.

(10) Patent No.: US 10,913,718 B2
(45) Date of Patent: Feb. 9, 2021

(54) SYNTHESIS AND CHARACTERIZATION OF METAL ORGANIC FRAMEWORKS

(71) Applicant: King Abdullah University of Science and Technology, Thuwal (SA)

(72) Inventors: Mohamed Eddaoudi, Thuwal (SA); Dongxu Xue, Thuwal (SA); Ryan Luebke, Thuwal (SA); Vincent Guillerm, Thuwal (SA); Abdul Malik Puthan Peedikakkal, Thuwal (SA); Karim Adil, Thuwal (SA); Lukasz Weselinski, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 16/396,905

(22) Filed: Apr. 29, 2019

(65) Prior Publication Data

US 2019/0248742 A1 Aug. 15, 2019

Related U.S. Application Data

(62) Division of application No. 15/314,445, filed as application No. PCT/US2015/032441 on May 26, 2015, now Pat. No. 10,273,209.

(60) Provisional application No. 62/002,950, filed on May 26, 2014.

(51) Int. Cl.

| | | |
|---|---|---|
| *C07D 209/88* | (2006.01) | |
| *B01J 20/22* | (2006.01) | |
| *B01J 31/16* | (2006.01) | |
| *C07C 63/66* | (2006.01) | |
| *C07C 65/05* | (2006.01) | |
| *C07C 65/11* | (2006.01) | |
| *B01J 37/04* | (2006.01) | |
| *B01J 37/06* | (2006.01) | |
| *C07D 317/36* | (2006.01) | |

(52) U.S. Cl.
CPC .......... *C07D 209/88* (2013.01); *B01J 20/226* (2013.01); *B01J 31/1691* (2013.01); *B01J 37/04* (2013.01); *B01J 37/06* (2013.01); *C07C 63/66* (2013.01); *C07C 65/05* (2013.01); *C07C 65/11* (2013.01); *C07D 317/36* (2013.01); *B01J 2231/34* (2013.01); *B01J 2531/0211* (2013.01); *B01J 2531/36* (2013.01); *B01J 2531/38* (2013.01); *B01J 2531/845* (2013.01); *Y02C 20/40* (2020.08)

(58) Field of Classification Search
CPC .. C07D 209/88; C07D 317/36; B01J 31/1691; B01J 37/04; B01J 37/06; B01J 2231/34; B01J 2531/0211
See application file for complete search history.

(56) References Cited

U.S. PATENT DOCUMENTS

| | | |
|---|---|---|
| 7,652,132 B2 | 1/2010 | Yaghi et al. |
| 7,799,120 B2 | 9/2010 | Yaghi |
| 9,266,907 B2 | 2/2016 | Xue |
| 9,920,076 B2 | 3/2018 | Eddaoudi |
| 10,253,048 B2 | 4/2019 | Eddaoudi et al. |
| 2004/0225134 A1 | 11/2004 | Yaghi et al. |
| 2007/0068389 A1 | 3/2007 | Yaghi |
| 2009/0198079 A1 | 8/2009 | Schubert et al. |
| 2009/0281341 A1 | 11/2009 | Schubert et al. |
| 2010/0072424 A1 | 3/2010 | Petoud et al. |

FOREIGN PATENT DOCUMENTS

| | | |
|---|---|---|
| JP | 2007516221 | 6/2007 |
| JP | 2011509825 | 3/2011 |
| WO | 2007035596 | 3/2007 |
| WO | 2009035664 | 3/2009 |
| WO | 2009133366 | 11/2009 |
| WO | 2009/154374 | 12/2009 |
| WO | 2012131483 | 10/2012 |

OTHER PUBLICATIONS

Zhang et al., Inorg. Chem. 2013, 52, 13332-13340. (Year: 2013).*
Communication under Rule 164(2)(a) EPC for EP Application No. 15745263.2 dated Mar. 21, 2019.
International Search Report and Written Opinion for International Application No. PCT/US2015/032441 dated Jan. 12, 2016, 20 pages.
Partial International Search Report for International Application No. PCT/US2015/032441 dated Oct. 28, 2015, 9 pages.
International Search Report and Written Opinion for International Application No. PCT/US14/54224 dated Nov. 4, 2014, 7 pp.
Bhattacharya, "Stabilization of 0-Mn-0 clusters (Mn5) in three dimensionally extended MOF structures: synthesis, structure and properties", CrystEngComm, vol. 14, No. 13, 2012, 4323-4334.
Bon, et al., "Zr(IV) and Hf(IV) based metal-organic frameworks with reo-topology", Chemical Communications, 2012, 48, pp. 8407-8409.

(Continued)

*Primary Examiner* — Robert S Cabral
(74) *Attorney, Agent, or Firm* — Billion & Armitage; Lisbeth C. Robinson

(57) ABSTRACT

A molecular building block composition can include a metal ion component; and a ligand component including a core including at least one functional group associated with the metal ion component and the core.

17 Claims, 24 Drawing Sheets

(56) References Cited

OTHER PUBLICATIONS

Cavka, et al. "A New Zirconium Inorganic Building Brick Forming Metal Organic Frameworks with Exceptional Stability", J. Am. Chem. Soc., vol. 130, No. 42, 2008, 13850-13851.
Das, et al., "A hexanuclear cerium(IV) cluster with mixed coordination environment", Inorganic Chemistry Communications, 2010, pp. 793-795.
Dekrafft, et al., "Zr- and Hf-based nanoscale metal-organic frameworks as contrast agents for computed tomography", Mater Chem., Jan. 1, 2012, pp. 18139-18144.
Deng, et al., "A series of three-dimensional lanthanide metal-organic frameworks with biphenylethene-4, 4'-dicarboxylic acid: Hydrothermal syntheses and structures+", CrystEngComm, 12, 2010, 1526-1535.
Eddaoudi, et al., "Systematic Design of Pore Size and Functionality in Isoreticular MOFs and Their Application in Methane Storage", Science, vol. 295, Jan. 18, 2002, 469-472.
Falaise, et al., "Three-Dimensional MOF-Type Architectures with Tetravalent Uranium Hexanuclear Motifs (U6O8)", Chem. Eur. J. 2013, 19, 5324-5331.
Fang, et al., "A series of Lanthanide-Based Cluster Organic Frameworks made of Heptanuclear Trigonal-Prismatic Cluster Units", Inorganic Chemistry, 52, Dec. 12, 2012, 6-8.
Feng, et al., "Metal-Organic Frameworks Based on Previously Unknown Zr8/Hf8 Cubic Clusters", Inorganic Chemistry, vol. 52, Oct. 22, 2013, 12661-12667.
Feng, et al., "Zirconium-Metalloporphyrin PCN-222: Mesoporous Metal-Organic Frameworks with Ultrahigh Stability as Biomimetic Catalysts", Angew. Chem. Int. Ed. 2012, 51, 10307-10310.
Ferrer, et al., "One-Dimensional Metal-Organic Framework with Unprecedented Heptanuclear Copper Units", Inorganic Chemistry, 46, 2007, 372-374.
Gandara, et al., "Isolated Hexanuclear Hydroxo Lanthanide Secondary Building Units in a Rare-Earth Polymeric Framework Based on p-Sulfonatocalix[4] arene", Crystal Growth & Design, vol. 10, No. 1, 2010, 128-134.
Garibay, et al., "Isoreticular synthesis and modification of frameworks with the UiO-66 topology", Chem. Commun., 2010, 46, 7700-7702.
Gross, et al., "Mono-, Di-, and Trimetallic Methacrylate-substituted Metal Oxide Clusters Derived from Hafnium Butoxide", Monatshefte f€ur Chemie 134, 1053-1063 and Erratum (2003).
Guillerm, et al., "A Series of Isoreticular, Highly Stable, Porous Zirconium Oxide Based Metal—Organic Frameworks", Angew. Chem. Int. Ed. 2012, 51, 9267-9271.
Guillerm, et al., "A zirconium methacrylate oxocluster as precursor for the low-temperature synthesis of porous zirconium(IV) dicarboxylates", Chem. Commun., 2010, 46, 767-769.
Hennig, et al., "Structure and stability range of a hexanuclear Th(IV)-glycine complex", Dalton Trans., 2012, 41, 12818-12823.
Kickelbick, et al., "Oxozirconium Methacrylate Clusters: Zr6(OH)4O4(OMc)12 and Zr4O2(OMc)12 (OMc = Methacrylate)", Chem. Ber. Recueil,1997,130,473-477.
Kickelbick, et al., "Variations in capping the Zr6O4(OH)4 cluster core: X-ray structure analyses of [Zr6(OH)4O4 (OOC-CH=CH2)10]2(mu-OOC-CH=CH2)4 and Zr6(OH)4O4(OOCR)12(PrOH) (R=Ph, CMe=CH2)", Inorganica Chimica Acta 284, 1999, 1-7.
Kim, et al., "Postsynthetic Ligand and Cation Exchange in Robust Metal-Organic Frameworks", J. Am. Chem. Soc. 2012, 134, 18082-18088.
Knope, et al., "Thorium(IV) Molecular Clusters with a Hexanuclear Th Core", Inorg. Chem. 2011, 50, 9696-9704.
Kogler, et al., "Control of the ratio of functional and non-functional ligands in clusters of the type Zr6O4(OH)4 (carboxylate)12 for their use as building blocks for inorganic-organic hybrid polymers", J. Mater. Chem., 2004, 14, 3133-3138.
Li, et al."Design and synthesis of an exceptionally stable and highly porous metal-organic framework", Nature, vol. 402, Nov. 18, 1999, 276-279.
Mereacre, et al., "Homo- and Heterovalent Polynuclear Cerium and Cerium/Manganese Aggregates", Helvetica Chimica Acta, vol. 92, 2009, 2507-2524.
Morris, et al., "Synthesis, Structure, and Metalation of Two New Highly Porous Zirconium Metal-Organic Frameworks", Inorg. Chem. 2012, 51, 6443-6445.
Nouar, et al., "Supermolecular Building Blocks (SBBs) for the Design and Synthesis of Highly Porous Metal-Organic Frameworks", J. Am. Chem. Soc., 2008, 130, 1833-1835.
Puchberger, et al., "Can the Clusters Zr6O4(OH)4(OOCR)12 and [Zr6O4(OH)4(OOCR)12]2 Be Converted into Each Other?", Eur. J. Inorg. Chem. 2006, 3283-3293.
Schaate, et al., "A Novel Zr-Based Porous Coordination Polymer Containing Azobenzenedicarboxylate as a Linker", Eur. J. Inorg. Chem. 2012, 790-796.
Schaate, et al., "Modulated Synthesis of Zr-Based Metal-Organic Frameworks: From Nano to Single Crystals", Chem. Eur. J. 2011, 17, 6643-6651.
Schaate, et al., "Porous Interpenetrated Zirconium-Organic Frameworks (PIZOFs): A Chemically Versatile Family of Metal-Organic Frameworks", Chem. Eur. J. 2011, 17, 9320-9325.
Takao, et al., "First Hexanuclear UIV and ThIV Formate Complexes—Structure and Stability Range in Aqueous Solution", Eur. J. Inorg. Chem. 2009, 4771-4775.
Wang, et al., "Stepwise assembly of metal-organic framework based on a metoal-organic polyhedron precursor for drug delivery", Chem. Commun., vol. 47, 2011, pp. 7128-7130.
Wissmann, et al., "Modulated synthesis of Zr-fumarate MOF", Microporous and Mesoporous Materials, 152, 2012, 64-70.
Xue, et al., "Tunable Rare-Earth fcu-MOFs: A Platform for Systematic Enhancement of CO2 Adsorption Energetics and Uptake", J. Am. Chem. Soc., vol. 135,, Apr. 22, 2013, 7660-7667.
Xue, et al., "Tunable Rare-Earth fcu-MOFs: A Platform for Systematic Enhancement of CO2 Adsorption Energetics and Uptake", Journal of the American Chemical Society, 135, May 22, 2013, 7660-7667.
Zhai, et al., "Coligand Modulated Six-, Eight-, and Ten-Connected Zn/Cd-1,2,4 Triazolate Frameworks based on Mono-, Bi-, Tri-, Penta-, and Heptanuclear Cluster Units", Crystal Growth & Design, vol. 7, No. 11, Aug. 7, 2007, 2332-2342.
Zheng, et al., "Synthesis and characterization of two Novel Lanthanide Coordination Polymers with an Open Framework Based on an Unprecedneted [Ln7(u3-OH)8]13 Cluster", Inorganic Chemistry, 2004, pp. 1600-1602.

* cited by examiner

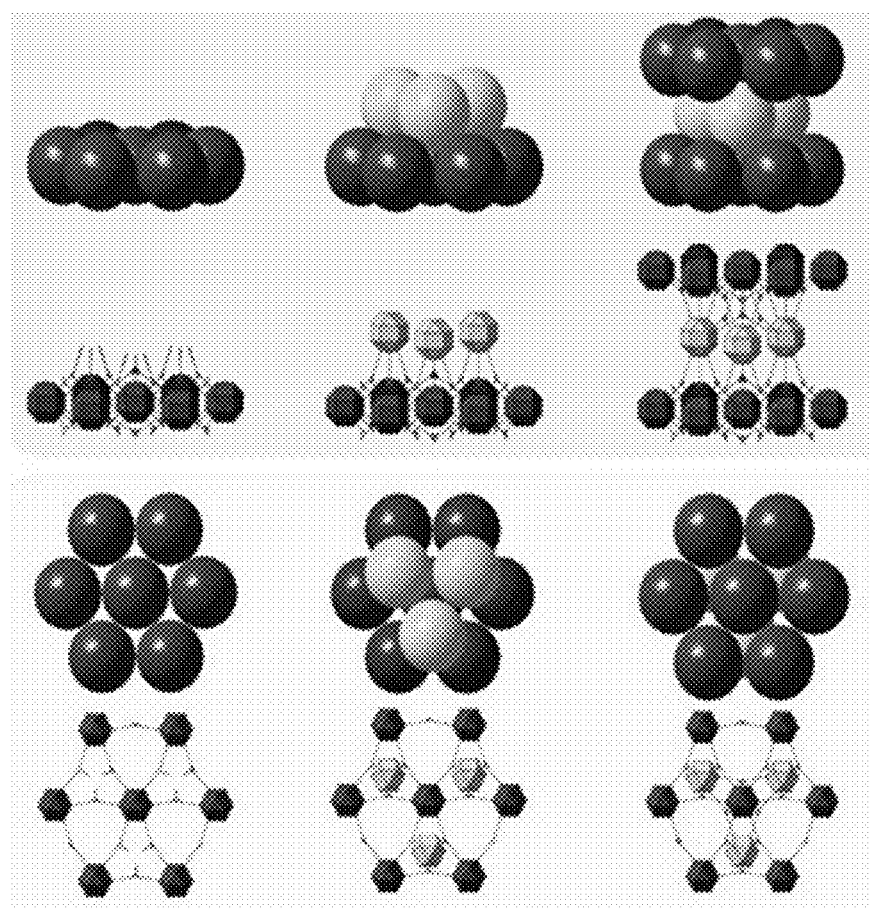
*FIG 5B*
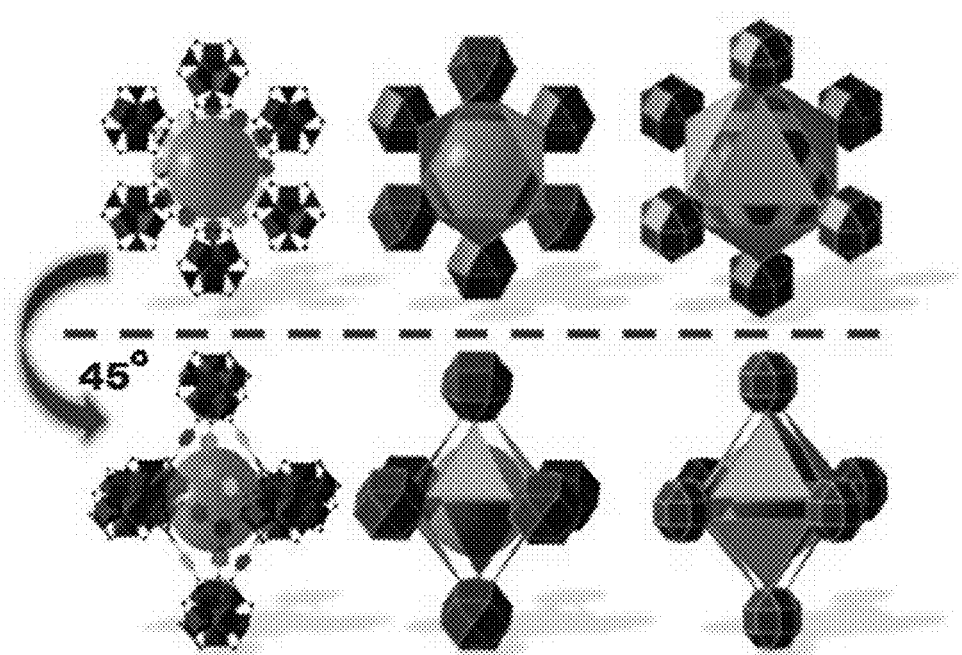
*FIG 6*  gea-MOF-1   gea-a net   rht-a net

| MBB | Ligand type | Example(s) of ligand | Resulting topology & connectivity | Illustration |
|---|---|---|---|---|
| A | 1 | | bcu 6-c | |
| A | 2 | | pcu 6-c | |
| A | 2 | | Novel 8-c | - |
| A | 3 | | Novel (3,8)-c | - |
| A | 4 | | scu (4,8)-c | |
| B | 1 | | fcu 12-c | |

*FIG 14A*

| MBB | Ligand type | Example(s) of ligand | Resulting topology & connectivity | Illustration |
|---|---|---|---|---|
| B | 1 | | hex 8-c | |
| B | 2 | | pcu 6-c | |
| B | 2 | | Novel | |
| B | 2 | | hxl 6-c | |
| B | 4 | | ftw (4,12) | |
| B | 4 | | Novel (3,12) | |
| C | 2 | | Novel (5,14)-c | |
| A+D | 3 | | Novel pek (3,8,12) | |
| D | 4 | | shp (4,12)-c | |

*FIG 14B*

| MBB | Ligand type | Example(s) of ligand | Resulting topology & connectivity | Illustration |
|---|---|---|---|---|
| E | 3 | 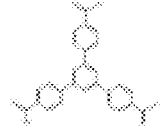 | Novel gea (3,18)-c | |
| A+E | 2 |  | Novel (8,18)-c | |
*FIG 14C*

| Metal ion | Ligand and abbreviation[a] | Topology | MBB and connectivity |
|---|---|---|---|
| Y | Br-bdc | fcu | 1, 12-c |
| Y, Tb, Eu, Gd | NH$_2$-bdc | fcu | 1, 12-c |
| Eu | (NH$_2$)$_2$-bdc | fcu | 1, 12-c |
| Y, Tb, Eu | (OH)$_2$-bdc | | |
| Eu, Gd, Tb | NO$_2$-bdc | fcu | 1, 12-c |
| Eu | 2,6-ndc | fcu | 1, 12-c |
| Y | edba | fcu | 1, 12-c |
| Tb | bpdc | fcu | 1, 12-c |

FIG 15A

| | | | |
|---|---|---|---|
| Y | 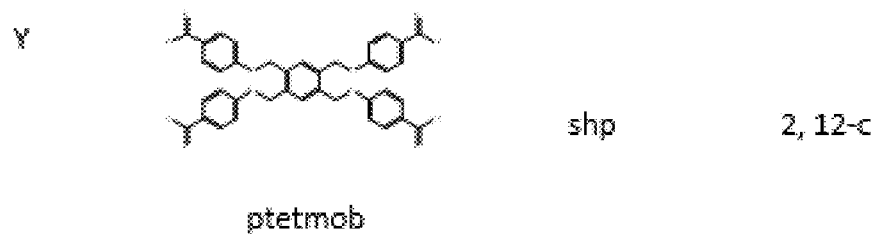 ptetmob | shp | 2, 12-c |
| Y |  TDC | Novel topology | 1, 8-c |
| Eu, Tb and Y | 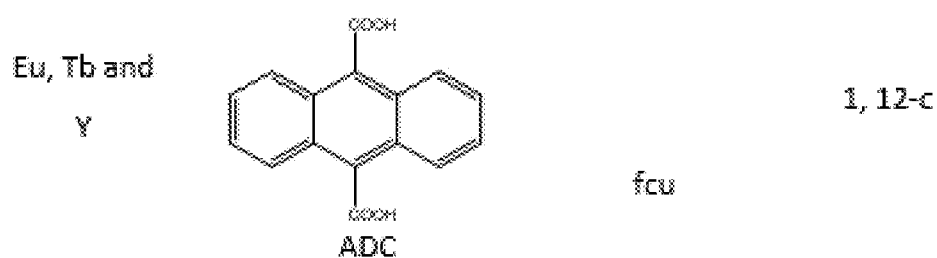 ADC | fcu | 1, 12-c |
*FIG 15F*

Tb 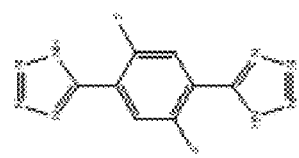 fcu 1, 12c
2,5-DFPBTZ
Tb 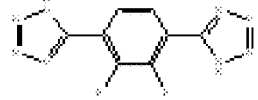 1, 12c
fcu
2,3-DFPBTZ
FIG 15G

SYNTHESIS AND CHARACTERIZATION OF METAL ORGANIC FRAMEWORKS

CROSS-REFERENCE TO RELATED APPLICATION

This application is a divisional application of U.S. application Ser. No. 15/314,445, filed on Nov. 28, 2016, which is a national stage entry of International Application No. PCT/US2015/032441, filed on May 26, 2015, which claims benefit of U.S. Provisional Application No. 62/002,950, filed on May 26, 2014, which applications are incorporated herein by reference.

BACKGROUND

Metal organic frameworks (MOFs) are considered a promising class of porous materials that are positioned to address many enduring societal challenges pertaining to energy and environmental sustainability, due to the prospective ability to mutually control their porous system structure, composition, and functionality. The inherent structural modularity (e.g., use of different metals, extensive library of organic building blocks with various shapes and dimensions, postsynthetic modifications, etc.) and exceptional controlled porosity place MOFs as ideal candidate materials for various relevant applications, such as gas separation, gas storage, drug delivery, catalysis and chemical sensing. However, the rational understanding of their assembly is still in its infancy, and as such, many paths remain to be explored to achieve made-to-order MOFs-stable materials specifically designed for particular applications.

BRIEF DESCRIPTION OF THE DRAWINGS

FIG. 5A-B illustrate the resultant gea-MOF-1 revealing hexagonal close packing, according to some embodiments.

FIG. 6 illustrates a geometric representation of gea-MOF-1, gea-a net, and rht-a net topologies, according to some embodiments.

FIGS. 14A-14C include a table showing examples of molecular building blocks (MBB), according to one or more embodiments of the present disclosure.

FIGS. 15A-15G include a table showing a list of examples of materials that have been synthesized and characterized, according to one or more embodiments of the present disclosure.

DETAILED DESCRIPTION

Metal Organic Frameworks (MOFs) are a class of materials recognized for their flexibility with regard to structural design which allows for a high degree of synthetic control over porosity and pore size. Through ligand modification or functionalization, the environment in the internal pores can be modified to suite specific applications. MOFs have shown great promise in the areas of gas storage, gas separation as well as in catalysis. MOFs can be porous and can be particularly well suited for gas storage and separation applications.

Over the past decade, the research community has witnessed the prominent growth of MOFs at the forefront of solid-state chemistry. MOFs offer a high degree of structural and functional tunability that is not available with other conventional porous materials (e.g. zeolites, activated carbons). The resultant structural modularity (e.g. use of different metals, reticular chemistry, post-synthetic modifications, etc.) and exceptional controlled porosity place MOFs as ideal candidate materials to address many enduring societal challenges pertaining to energy and environmental sustainability. One of the ongoing challenges in MOF chemistry is predicting the structure or framework topology resulting from a selected combination of MOF precursors (metal salts and organic ligands). MOFs can be synthesized from building blocks or clusters of high connectivity. Such highly connected building blocks can be attractive targets due to the limited number of possible topological outcomes which leads to a greater degree of predictability in structure.

The molecular building block (MBB) approach has recently emerged as a powerful strategy for the design and construction of solid-state materials and to target MOFs with given topologies, e.g. based on edge transitive nets. The molecular building block joins or otherwise associates with other molecular building blocks to form supramolecular structures. The molecular building block can be connected by different numbers, such as 8, 10, 12, 14, or 18 connected. For example, a 12-connected molecular building block can have 12 sites for ligand attachment to neighboring structures. Metal-organic framework (MOF) materials can have tunable properties based on their structure, including porosity. Unique porous structures can allow the material to be used in applications including gas sequestration, storage and separation or scrubbing.

Figures 1A, 1B:
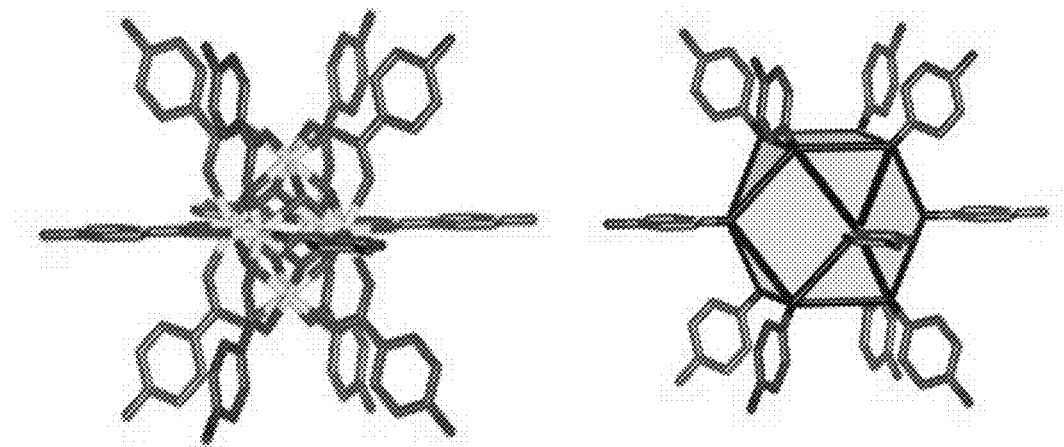
FIG. 1A illustrates a hexanuclear 12-c cuboctahedral Molecular Building Block (MBB), according to some embodiments.
FIG. 1B illustrates a cuboctahedral geometric representation of 12-c hexanuclear cluster, according to some embodiments.

Structures having highly connected clusters are becoming more common and interest has been shown in the group IV (Zr and Hf) hexanuclear 12-connected molecular building block (MBB) having cuboctahedral geometry (FIG. 1A). This increased interest can be attributed to the high degree of thermal and chemical stability seen in many of the MOFs, for example, MOFs composed of 12-c MBB.

Discrete clusters can be described with zirconium, hafnium, and cerium, uranium, and thorium, in some embodiments. Examples of MOFs include Zr fcu: 1,4-BDC, TPDC, $NH_2$-TPDC, MUCO, FUM, BPDC, $NH_2$—BDC, $NO_2$—BDC, Br-BDC, AzoBDC, 1,4-NDC, 2,6-NDC, $Cl_2$AzoBDC, $HO_2C[PE-P(R_1,R_2)-EP]CO_2H$ (R=H, OMe, OPent, dodec, $O(CH_2CH_2O)_2Me$, $OCH_2CCH$, $OCH_2CCTIPS$), etc.; Hf fcu: 1,4-BDC; U fcu: BPDC, BDC, 2,6-NDC and fum; Zr—Ti (mix metal) fcu: 1,4-BDC; —Zr, Hf reo: dttp; Zr csq: $H_4$-TCPP-$H_2$; Zr ftw: $H_4$-TCPP-$H_2$, $H_4$—XF.

The successful implementation of the MBB approach for the design and construction of MOFs can have several requirements. For example, 1) selection of an ideal blueprint net that is exclusive for the assembly of its corresponding basic building units, and 2) isolation of the reaction conditions that consistently allow the in situ formation of the desired inorganic MBB, matching the augmented basic building units of the targeted net.

Uninodal and binodal nets with high connectivity, that is having at least one node >8, can be suitable targets in crystal chemistry, as they offer more limited options for the assembly of highly connected MBBs. Some systems can permit the isolation of new highly-connected polynuclear clusters that are amenable to the formation of novel MOF platforms. The difficulty to isolate reaction conditions that permit the formation of highly-connected MBBs (i.e., >12) is directly correlated to the scarce number of MOFs with high connectivities. Simple MBBs with connectivity of 8 or greater can be too intricate to be systematically obtained by means of simple organic ligands or polynuclear clusters. However, such complex and elaborate building blocks can be designed and attained as supermolecular building blocks (SBBs), larger building units composed of interlinked smaller MBBs. Utilization of these SBBs with a high degree of symmetry and connectivity as well as the needed elaborate directional and structural information, permits access to other MOF platforms, as demonstrated by the use of 24-connected metal-organic polyhedra (MOPs) as SBBs for the intended formation of highly connected rht-MOFs.

As disclosed herein, MBBs comprise a cluster of metal ions and clustering precursor moiety. The clustered precursor and metal ions can also be referred to as a metal cluster. Metal clusters are polynuclear, and contain a plurality of metal ions. Metal clusters can contain at least 6 metal ions, at least 7 metal ions, at least 8 metal ions, at least 9 metal ions, at least 10 metal ions, at least 11 metal ions, at least 12 metal ions, at least 13 metal ions, at least 14 metal ions, at least 15 metal ions, at least 16 metal ions, at least 17 metals or at least 18 metal ions, for example.

MOFs can include metal ions and ligand that can include a core. A core can include an aryl, a heteroaryl, a carbocyclyl, or a heterocyclyl. The core can include one or more coordination groups. A coordinating group can be anionic, such as carboxylate, tetrazole, triazole (including protonated versions), sulfonate, and so on. A coordinating group can include electron donors, such as nitrogen donor: pyridine, pyrimidine, triazole, carbonyl based oxygen donor, or sulfur based donor.

Coordinating groups can coordinate in a monodentate fashion, a bis monodentate fashion, or a bidentate fashion. In some embodiments, coordinating groups can coordinate in a polydentate fashion.

A molecular building block can include a metal cluster. The metal can be any rare earth metal, in some embodiments. The metal can have single type of metal component or the metal can be a mixture of multiple metals. In one example, the mixture includes one or more rare earth metals.

Ligands can coordinate or associate to form a 2-18 connected cluster. Connectivity of clusters can be based upon the number of polyfunctional ligands (as described herein) which are coordinated to the cluster. The ligands can coordinate to the cluster through a functional group. An exemplary metal cluster can have a form of $M_6$ $(OH)_8$-x $O_X$ (Coordinating Group 1)$_Z$ (Coordinating Group 2)$_{12-z}$. This cluster (and ligand) can form a metal organic framework having the composition of $M_6(OH)_{8-x}$ $O_X$(Ligand)$_Y$. Y can be any value from 2 to 12; X can be any value from 0 to 8; Z can be any value from 2 to 12.

A metal cluster can have a form of $M_9$ $(OH)_{11-x}$ $O_X$ (Coordinating Group 1)$_Z$ (Coordinating Group 2)$_{12-z}$. This cluster (and ligand) can form a metal organic framework having the composition of $M_9(OH)_{11-x}O_X(L)_Y$. The metal cluster can have additional solvents or counter ions associated with it. These can be water, dimethyl formamide, dimethyl amine, formate, or a molecule with a coordinating group.

A metal organic framework can have various network topologies based on the connectivity of the cluster and the ligand. For example, the connectivity can be 12-connected, 4,12-connected, 4,8-connected, 6-connected, 3,8 connected, 8-connected, or 3,18-connected. Connectivity can also include z-connected (z can be any integer from 3 to 18) or x,z-connected (x can be any integer from 3 to 6) and (z can be any integer from 3 to 18), or x,y,z-connected (x can be any integer from 3 to 6) and (y can be any integer from 3 to 18) (z can be any integer from 3 to 18).

There has been a strong scientific drive to minimize greenhouse gas emissions especially $CO_2$. The release of $CO_2$ from flue gas and the automobile industry are the major contributors, and myriad efforts are underway to economically separate and capture the effluent $CO_2$. Highly porous sorbent materials have emerged as a plausible solution, and considerable efforts have been put forth to develop suitable materials. An optimal adsorbent for $CO_2$ separation should, in addition to high adsorption uptake and suitable kinetics, exhibit high affinity toward $CO_2$ to be translated into high interaction, which in turns plays a critical role in determining the adsorption selectivity and the energy required to release $CO_2$ during the regeneration step. Accordingly, the ideal isosteric heat of adsorption ($Q_{st}$) should permit reversible physical adsorption-desorption operation in a pressure or vacuum swing adsorption (PSA or VSA) process (i.e., $CO_2$-sorbent interactions are neither too strong nor too weak).

MOFs appear well-poised to address the $CO_2$ challenge due to their mild synthesis conditions, relatively high thermal stability, large pore volumes, potentially exposed inner surface with high localized charge density, and readily programmable and modular construction (i.e., a given structure with the desired net topology; functionalizable isoreticular structures) from pre-designed molecular building blocks (MBBs). As such, considerable effort has been dedicated to ascertaining the ideal $CO_2$-MOF interactions/energetics, but minimal systematic studies of finely-tuned MOFs have been reported.

Development and isolation of novel MBBs can facilitate the rational construction of targeted functional MOFs. The discovery of novel modular and rigid inorganic MBBs and establishing reaction conditions that permit to generate a specific inorganic MBB consistently in situ can be a vital criterion/prerequisite for the prospective design and rational construction of desired MOFs.

With the aim to construct porous MOFs with high localized charge density, a potential attribute to promote/enhance the $CO_2$ sorption energetics, porous MOFs with high localized charge density, a potential attribute to promote/enhance the $CO_2$ sorption energetics, can be prepared based on metal-ligand directed assembly of electron-rich RE metal ions and non-centrosymmetric hetero-functional ligands containing carboxylate and terazolate moieties. Hexanuclear RE-based ($Tb^{3+}/Y^{3+}$) MBBs, generated in situ, to construct a series of 12-connected MOFs can possess face centered cubic (fcu) topology. The MBBs are bridged in a linear fashion through an assortment of fluoro and/or tetrazolate functionalized organic ligands, as outlined in Scheme 1. Systematic gas sorption studies on these materials have elucidated the effects of distinctive parameters on $CO_2$-MOF sorption energetics.

A MOF can potentially be porous. The pore size can range from 3 Å-100 Å. An MOF can potentially adsorb or absorb gases (atoms or molecules). These gases can be monatomic gases (atoms), such as He, Ne, Ar, Kr, Xe, or Rn. These gases can be diatomic gases (molecules), such as $N_2$, $O_2$, $H_2$, or $I_2$. These gases can be polyatomic gases, such as $CO_2$, $H_2S$, $H_2O$, or hydrocarbons. Hydrocarbons can be linear, branching or aromatic. Hydrocarbons can be heterocyclic. Hydrocarbons may or may not have 1 or more additional functional groups including —OH, —Cl, —F, and so on.

A metal organic framework can potentially selectively adsorb, absorb, separate different types of gases, atoms or molecules. The gases, atoms or molecules that can be separated include any gas that can potentially be adsorbed/absorbed.

A method for making a metal organic framework can include combining ligand and metal. Metal can be any rare earth metal, in some examples. Metal source can be a metal salt; the metal salt can have the anion of $NO_3$, $SO_4$, $BF_4$, $CO_3$, Cl, and so on. Metal source can be a metal oxide; metal source can be elemental metal (oxidation state 0); the oxidation state of the metal source can be (0, +1, +2, +3, +4).

The method can include using a modulator or structure directing agent (SDA). SDA can include a molecule which promotes the formation of the inorganic building block. SDA can include a coordinating group. An SDA can include a fluorine group, such as fluorinated organic acids, fluorobenzoic acid. An SDA can contain 1 or more fluorines. A fluorine may be a fluorinated group, for example.

Single fluorine can be in the 2, 3, or 4 position. Multiple fluorines can be in any position on the ring. Other functional group(s), such as alkyl, —OH, $NH_2$, $NO_2$, can be on the ring.

An SDA can include fluoro alkyl acids, which can have more than 1 carbon, can be saturated or unsaturated, or can have 1 or more fluorine. Fluorine can be in any position on alkyl chain. An SDA can include fluoro acetic acids, which can have 1 fluorine, 2 fluorines, or 3 fluorines.

Synthesis of MOFs can involve combining ligand, and a metal source. The synthesis may include one or more solvents. The synthesis may include one or more SDA. The reaction may be heated during synthesis. Heating may be done in an oven. Heating may be done in a microwave reactor.

In one example, a metal organic framework composition comprises a metal ion component; and a bidentate ligand component having two anionic binding groups, wherein the two anionic binding groups are oriented 180 degrees from each other; wherein the metal ion component and the bidentate ligand component associate to form a face-centered cubic network. In another example, a molecular building block composition can include a metal ion component and a ligand component including a core and at least one anionic group associated with the metal ion component and the core. The metal ion component and the ligand can associate to form a 4, 6, 8, 10, 12, 14, or 18 connected cluster. The core can include an aryl, a heteroaryl, a carbocyclyl, or a heterocyclyl.

Metal ions can form a metal ion component of a metal organic framework composition. The metal ion can be an electron rich metal ion. For example, the metal ion can be a RE metal ion, for example, a lanthanide element, such as an ion of La, Ce, Pr, Nd, Sm, Eu, Gd, Tb, Dy, Ho, Er, Tm, Yb, Lu, or Y. In certain circumstances, the metal ion is terbium or yttrium, e.g., $Tb^{+3}$ or $Y^{+3}$.

A bidentate ligand can form a bidentate ligand component of the metal organic framework composition. The bidentate ligand can have two anionic binding groups. The two anionic binding groups, point away from each other. Specifically, the two anionic binding groups can be oriented 180 degrees from each other. The bidentate ligand can have the structure:

$$A1\text{-}L\text{-}A2 \qquad (I)$$

In formula (I), each A1 can be carboxyl, tetrazolyl, sulfonyl, or phosphoryl;

In formula (I), each A2 can be carboxyl, tetrazolyl, sulfonyl, or phosphoryl;

In preferred embodiments, A1 and A2 are each, independently, carboxyl or tetrazolyl.

In formula (I), L can be a divalent aryl, heteroaryl, carbocyclyl, or heterocyclyl. In some embodiments, L can be a 3- to 14 membered divalent monocyclic heterocyclyl, a 3- to 14 membered divalent aryl, or a 3- to 14 membered divalent heteroaryl. In some embodiments, L is substituted with 1, 2, 3, or 4 halo or halomethyl groups. For example, L can be an ortho substituted fluoro phenylene, naphthylene or diphenylene group.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-8-membered monocyclic.

In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5, 6, 7, 8-tetrahydroquinoline and 6,7-dihydro-5H-pyrrolo[3,2-d]pyrimidine.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6 dimethylbicyclo[3.1.1] heptyl, 2,6,6-trimethylbicyclo[3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. Preferably the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

The term "arylalkyl" refers to an alkyl group substituted with an aryl group. Representative examples of arylalkyl groups include, for example, benzyl, picolyl, and the like.

The term "phenylene" refers to a divalent phenyl.

The molecular building block can include bridging ligands, such as, for example, oxy, hydroxyl, sulfhydryl, or amino groups.

In the synthesis of the molecular building blocks, the molecular building block can have an overall ionic charge. Thus the molecular building block can be an anion or a cation and have one or more corresponding counterions, such as, for example, $H^+$, $Li^+$, $Na^+$, $K^+$, $Mg^+$, $Ca^{2+}$, $Sr^{2+}$, ammonium (including monoalkyl, dialkyl, trialkyl or tetraalkylalkyl ammonium), or one or $F^-$, $Cl^-$, $Br^-$, $I^-$, $ClO^-$, $ClO_2^-$, $ClO_3$, $ClO_4^-$, $OH^-$, $NO_3$, $NO_2^-$, $SO_4^{2-}$, $SO_3^{2-}$, $PO_4^{3-}$, $CO_3^{2-}$, borate (including monoalkyl, dialkyl, trialkyl or tetraalkylalkyl borate) or $PF_6^-$, and organic counterions such as acetate or triflate.

The A1 and A2 groups are oriented at 180 degrees from each other. For example, when L is arylene, A1 and A2 are in a "para" or substantially "para" relative position. In a phenylene structure, A1 and A2 are at positions 1 and 4 on the ring; in a biphenylene structure, A1 and A2 are at positions 4 and 4'.

One method of making a MOF composition can include contacting a metal ion component with a bidentate ligand component having two anionic binding groups. A salt of the metal ion can be dissolved in a solvent and combined with the bidentate ligand. Optionally, other salts can be added to provide other counter ions in the final structure. The material is then crystallized from the combined solution. The presence of a hydrophobic group in the bidentate ligand, for example, a fluoro group ortho to the binding group, contributes to formation of a desired fcu structure. The bidentate ligand having a hydrophobic group can be present in a catalytic amount during formation of the final MOF.

Embodiments described show success in controlling the directionality of rare earth based inorganic MBBs by pioneering the use of fluorinated ligands and/or a modulators such as 2-fluorobenzoic acid (2-FBA). This strategy is used not only to promote the crystallization of the resultant MOF materials, but also to preclude the formation of the RE based inorganic chains-dominant infinite building units in RE-MOF chemistry due to the RE hard sphere behavior that offers only limited possibilities to control the directionality and dimensionality of coordinated carboxylate based ligands.

Some examples of groups of metals and organic ligands that can be used to synthesize MOFs:

Cluster 1: $M_6(OH)_{8-x}O_x(R_1COO)_{12-y}(R_2CN4)_y \cdot (H_2O)_z$ (x=0-8, y=0-12 z=0-6, M=Y, La—Lu, excluding Pm) (cluster 1).

Cluster 2: $M_9(OH)_{11-x}O_x(R_3COO)_{18-y-z}(CN_4)_y \cdot R'_z$ (x=0-11, y=0-18, z=0,6, M=Y, La—Lu, excluding Pm; R'=$H_2O$, DMF, DMA, formate, etc.) (cluster 2).

One molecular building block (MBB) can be a hexanuclear cluster 1. In case no topology is accessible with the selected organic ligand (that can be 2, 3, 4 or more connected) ligand, this cluster can transform in-situ into a nonanuclear cluster 2 to allow the formation of other 3-periodic structures. These two MBBs can be regarded as secondary building units (SBUs) for the assembly of 3 periodic networks. Therefore, these SBUs have specific connectivity, related to the number of points of extension they exhibits.

R1 can include an aryl, a heteroaryl, a carbocyclyl, or a heterocyclyl. R2 can include an aryl, a heteroaryl, a carbocyclyl, or a heterocyclyl. R3 can include an aryl, a heteroaryl, a carbocyclyl, or a heterocyclyl.

A discrete cluster (with Tb) can be isolated using a monocarboxylate ligand (2-fluoro benzoic acid). Cluster 1 can be 8, 10, 12, or 14 connected, and cluster 2 can be 12 and 18 connected. Examples include of 8-connected 12-connected, 14-connected SBUs built from hexanuclear cluster (top), and 12-connected, 18-connected SBUs built from nonanuclear cluster (bottom). There can be other connectivity as well. That makes this family of cluster very versatile as MBB for the construction of new MOFs, allowing the design of several different topologies.

Examples of MOFs containing one of these MBB (cluster 1 or cluster 2), or combination of several MBBs including at least cluster 1 or cluster 2 can be prepared. Tuning possibilities are multiples, at different levels, for example:
1) Varying the metal or combination of metals in the cluster (i.e. using Tb or Yb precursors, or using a mix of metal precursors 10% Tb and 90% Yb or any other combination);
2) Varying the length of the organic ligand;
3) Varying the shape (e.g. linear, bent, etc.);
4) Varying the polarity of the ligand (add amine, nitro, methyl groups, etc.);
5) Varying the connectivity of the ligand (1, 2, 3, 4, or higher connectivity);
6) Using multiple ligands in the same structure;
7) Varying the connectivity of the inorganic MBB; and
8) Presence of at least two different MBBs, including at least one cluster 1 or cluster 2.

Some MOF materials showed highly promising results for gas sorption/separation ($CO_2$, hydrocarbons, etc.). The high connectivity of the MBB may also improve their thermal/chemical stability. For instance, one of the fcu-MOFs can be stable up to at least 400° C. and maintains the structure in the boiling acid (pH=3.5 HCl aqueous) or basic (pH=13.5 NaOH aqueous) condition for 24 hours.

For the synthesis and design of MOFs, one important step to use the MBB approach is identification of conditions that will allow consistent in-situ formation of the inorganic MBB. In addition to group IV metals, rare earth (RE) metals can also form a similar hexanuclear cuboctahedral cluster, as shown in FIGS. 1A-B. FIG. 1A shows a hexanuclear 12-c cuboctahedral MBB $M_6(OH)_8L_{12}$, where M is a rare earth or group IV metal. FIG. 1B shows cuboctahedral geometric representation of 12-c hexanuclear cluster. For example, by linking these MBBs through ditopic carboxylate/tetrazole based ligands, Terbium and Yttrium based fcu-MOFs can be synthesized. It can, in some embodiments, be necessary to incorporate fluorine containing ligands or using F-Benzoic acid as a reaction modulator to promote the formation of the related 12-c MBB with rare earth metals.

Figure 2:
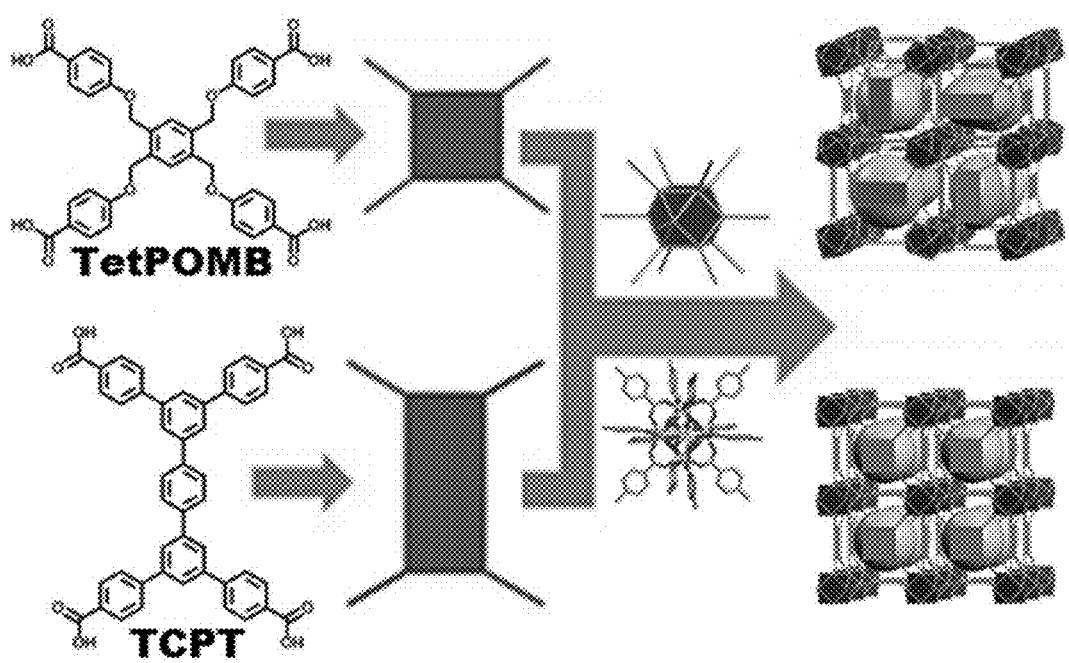
FIG. 2 illustrates a schematic showing the combination of 4-connected quadrangular ligands with a 12-connected Rare Earth (RE) based building block resulting in Metal Organic Framework (MOFs) with ftw-a topology, according to some embodiments.

A rare-earth (RE) based MOF platform can permit the isolation of appropriate reaction conditions for the consistent formation, in situ, of the RE hexanuclear cluster $[RE_6(\mu_3\text{-}OH)_8(O_2C\text{—})_{12-x}(N_4C\text{—})_x, x=0,8]$, a new 12-connected inorganic MBB ideal for MOF crystal chemistry. Such a 12-connected MBB (cuboctahedron building units) can be linked via 4-connected MBBs (square building units) or directly bridged to afford MOFs with ftw or fcu topologies, respectively. FIG. 2 is schematic showing the combination of 4-connected quadrangular ligands (PTetMOB or TCPT) with a 12-connected Rare Earth based building block resulting in MOFs with ftw-a topology. In utilizing the hexanuclear 12-c MBB to design a MOF having 12 connected nodes, the knowledge of the possible topological outcomes is vital. The focus can be on utilizing 4-c carboxylate based ligands to obtain RE MOFs with 12 and 4 connected nodes ((12,4) nets). There are a total of three known (12, 4-nets) which can potentially be obtained from this approach. Of the three (12, 4)-nets (shp, ftw, ith), the ftw network topology is the only one composed of 12-c nodes having the same (cuboctahedral) geometry as the 12-c hexanuclear MBB, as shown in FIGS. 1A-B. Thus RE MOFs having the ftw topology (ftw-MOFs) can be synthetically accessible materials and a likely outcome when combining 4-c and cuboctahedral 12-c MBBs. In addition to the proper geometry of the 12-c metal cluster, this topology is edge transitive. This can permit, synthetically, the use of a single type of link between nodes which can be accomplished by using a single type of ligand.

To prepare a rare earth (RE) ftw-MOF, a flexible tetracarboxylate ligand 4,4',4'',4'''-Phenyl-1,2,4,5-tetra methoxybenzoic acid (PTetMOB) can be used, as shown in FIG. 2, which can act as a square or quadrangular MBB.

The PTetMOB ligand was chosen was based upon the central phenyl ring constituting the ligand core, linked through the methoxy linkages to benzene carboxylic acid moieties. This linkage can provide sufficient rigidity to form open frameworks while simultaneously allowing flexibility to meet the geometrical requirements or constraints imposed by targeted topologies. The in-situ formation of the 12-c RE MBB can be facilitated by the addition of F-Benzoic acid, as a reaction modulator. This allows for the synthesis of single crystalline yttrium, ytterbium, and terbium ftw-MOF-1 analogs.

No topology has been found in the art regarding the assembly of a 12-connected MBB (points of extension matching the vertices of the cuboctahedron) with triangles, which can offer a great opportunity to discover other high-connected RE polynuclear clusters and their respective assembly into MOFs with potentially novel topologies.

MOFs constructed from RE metals ions and/or clusters can be great candidates for building multifunctional materials, due to their intrinsic properties (e.g., catalysis, etc.). However, their deliberate construction can be an on-going challenge due to the fact that the RE hard sphere behavior limits the structural directionality of coordinated ligands, and therefore it can be difficult to control their resulting MOF structure outcomes. In fact, only a few open RE carboxylate-based MOFs have been reported to date, many of which tend to collapse upon removal of the trapped/coordinated solvent molecules.

Utilizing certain methods as described herein, a RE nonanuclear carboxylate cluster can be formed, in situ. Such a cluster can include $[RE_9(\mu_3\text{-}OH)_8(\mu_2\text{-}OH)_3(O_2C\text{—})_{18}]$, (RE=Y, Tb, Er, Eu) which can serve as an 18-connected MBB for the assembly of a (3,18)-connected MOF with a gea topology, gea-MOF-1. This (3,18)-connected net can be an ideal blueprint for the deliberate construction of a second gea-MOF, gea-MOF-2, based on the SBB approach where the relatively simple 18-connected inorganic MBBs were replaced by more complex MOPs that act as a 18-connected SBBs.

Reaction conditions that permitted the isolation of the RE-based fcu-MOFs can be employed in the absence of bridging ligands (i.e. terminal ligands) in order to ensure the prospective formation of the corresponding discrete hexanuclear cluster.

Single crystals of molecular hexanuclear cluster can be grown and isolated, via prolonged slow evaporation of the reaction mixture. They can be formulated by single crystal diffraction (SCD) data as $[RE_6(\mu_3\text{-}OH)_8(O_2C\text{—}C_6H_4F)_{11}(DMF)(NO_3^-)(H_2O)_6]$ (RE=Tb). The conditions that permitted the formation of the RE-hexanuclear cluster (i.e. fcu-MOF based on a non-fluorinated ligands and discrete cluster) can entail the presence of 2-fluorobenzoic acid (2-FBA) in the reaction mixture. 2-FBA can play a major role in repelling water molecules and might explain the in situ formation of multinuclear clusters rather than infinite RE chains commonly observed in RE-MOFs.

The MBB, 12-connected RE-hexanuclear cluster, can be assembled with other polytopic linkers. The absence of reports regarding enumerated and listed binodal net for the combination of 3-connected (triangle vertex figure) and 12-connected (cuboctahedron vertex figure) nodes can suggest conceivable incompatibility of the newly isolated 12-connected RE-hexanuclear cluster with triangular ligands. In the predicted (3,12)-connected ttt net, the corresponding compatible 12-connected building block (truncated tetrahedron) can have a very different shape than a cuboctahedron. Due to the ability to form the 12-connected RE-hexanuclear clusters and their non-compatibility with triangular ligands, compatible polynuclear clusters have been pursued and achieved.

For example, a 1,3,5-benzene(tris)benzoate (BTB) ligand can be used as a vehicle to potentially unveil new highly-connected MOFs based on the assembly of a distinct highly-connected RE-nonanuclear clusters. This concept is demonstrated in a reaction between $H_3BTB$ and of $Y(NO_3)_3 \cdot 6H_2O$ in presence of 2-FBA in an N,N-dimethylformamide (DMF)/water solution yielded hexagonal rod shaped crystals, formulated as $(DMA^+)_2[Y_9(\mu_3\text{-}OH)_8(\mu_2\text{-}OH)_3((O_2C\text{—}C_6H_4)_3C_6H_3)_6]_n \cdot (solv.)_x$. Structural/topological analysis of the resulting crystal structure reveals the formation of a (3, 18)-connected MOF based on a novel RE polynuclear cluster $[RE_9(\mu_3\text{-}OH)_8(\mu_2\text{-}OH)_3(O_2C\text{—})_{18}]$, a distinctive 18-connected MBB linked to the triangular BTB to form a MOF with an unprecedented gea topology, where the carbon atoms of the coordinated BTB carboxylate moieties, acting as points of extension, coincide with the elongated triangular orthobicupola vertex figure of an unprecedented binodal (3,18)-connected net.

Figure 3:
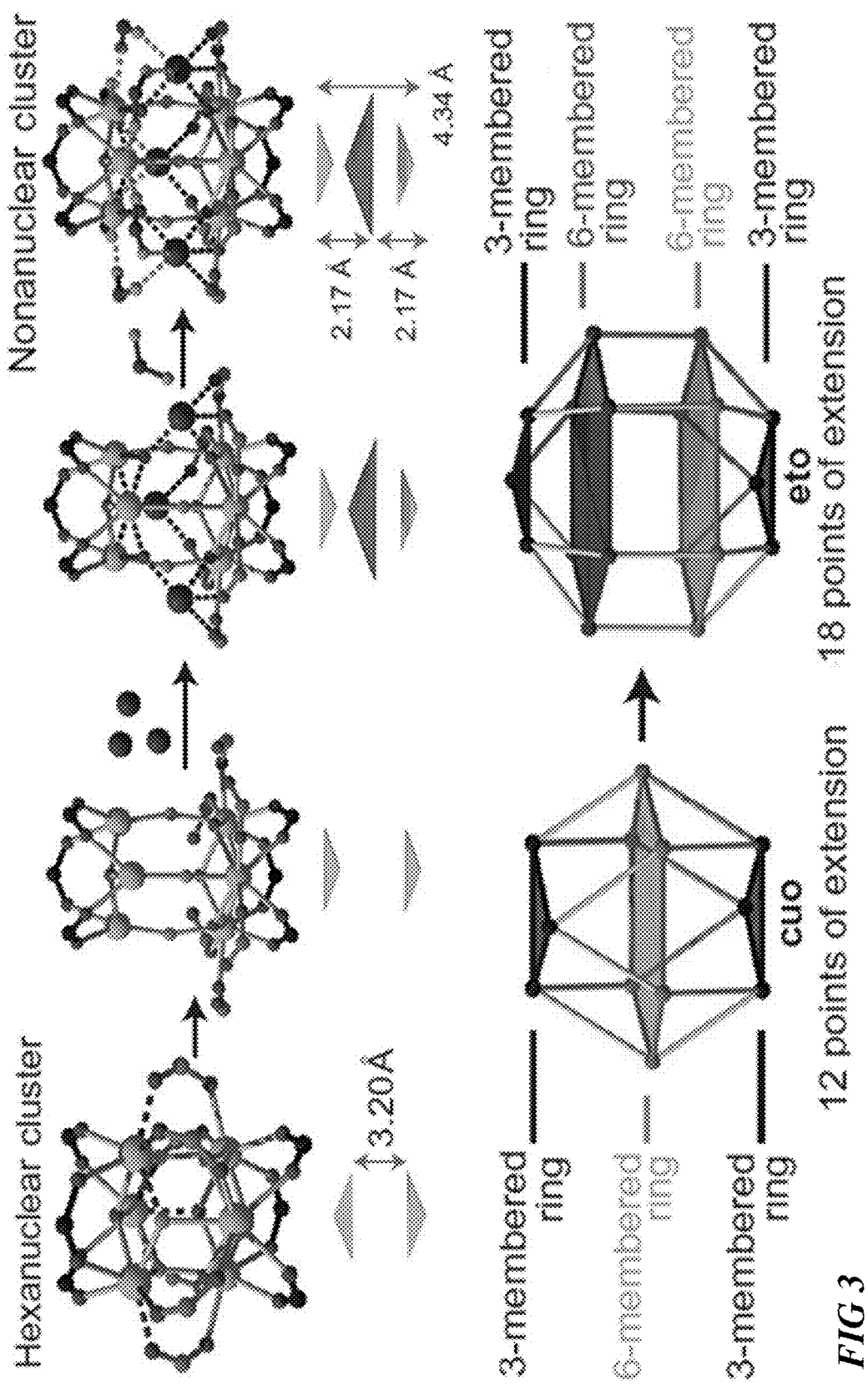
FIG. 3 illustrates the evolution from a hexanuclear cluster to a nonanuclear cluster, according to some embodiments.
Figure 4:
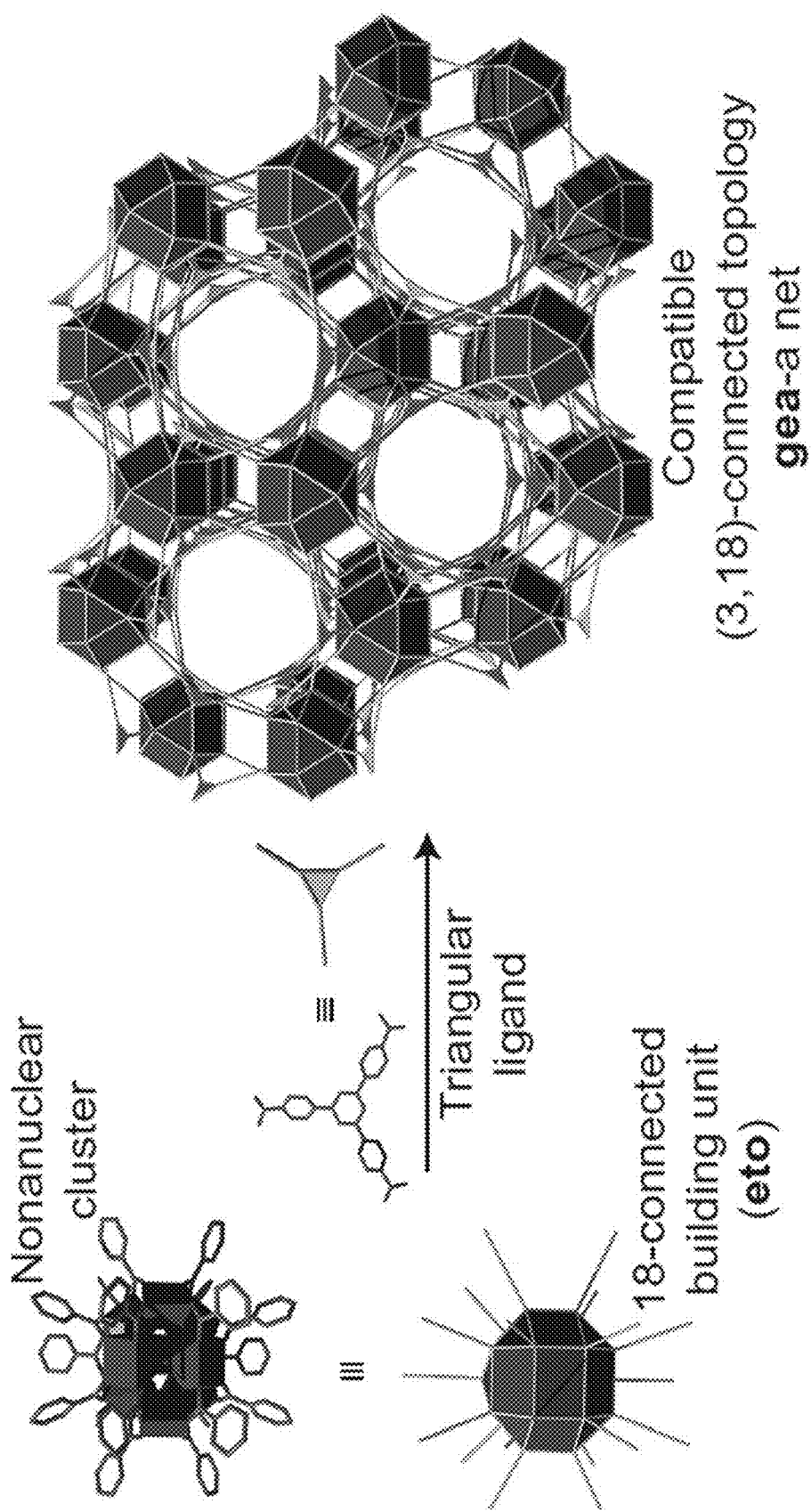
FIG. 4 illustrates a formation of a gea-MOF-1 by coordination of 18-connected MBBs with 1,3,5-benzene(tris) benzoate (BTB) ligands, according to some embodiments.

Analysis of the $[RE_9(\mu_3\text{-}OH)_8(\mu_2\text{-}OH)_3(O_2C\text{—})_{18}]$ cluster reveals its close relation to the $[RE_6(\mu_3\text{-}OH)_8(O_2C\text{—})_{12}]$ cluster, but three additional metals have been incorporated. A proposed path showing the evolution from a hexanuclear cluster to a nonanuclear cluster is shown in FIG. 3. The triangles represent the spatial arrangement of the RE atoms in the cluster and show the 30° rotation and addition of the three RE metal ions. The cage schematic demonstrates the effect of the cluster evolution on the MBB points of extension, which increase from 12 (cuo) to 18 (eto). This RE-MBB $[RE_9(\mu_3\text{-}OH)_8(\mu_2\text{-}OH)_3(O_2C\text{—})_{18}]$ (RE=Y, Tb, Er, Eu) can be built from nine metal ions arranged in a tri-capped trigonal prism (Johnson solid ($J_{51}$), tct symbol in RCSR database). Six of the Y ions are coordinated to eight oxygen atoms (i.e., 4 from the carboxylates, 3 $\mu_3$-OH and 1 $\mu_2$-OH) while the coordination mode of the remaining three sites is reduced to six (i.e., 4 O from the carboxylates and 2 $\mu_2$-OH). The overall cluster can be anionic, and the resultant framework overall charge can be balanced by dimethylamonium cations ($DMA^+$), generated in situ upon the decomposition of DMF solvent molecules. As shown in FIG. 4, the yttrium cluster is 18-connected MBB, elongated triangular orthobicupola (eto) building unit with 18 vertices, and is coordinated by eighteen carboxylates from eighteen different BTB ligands to form a gea-MOF-1.

Figure 5A:
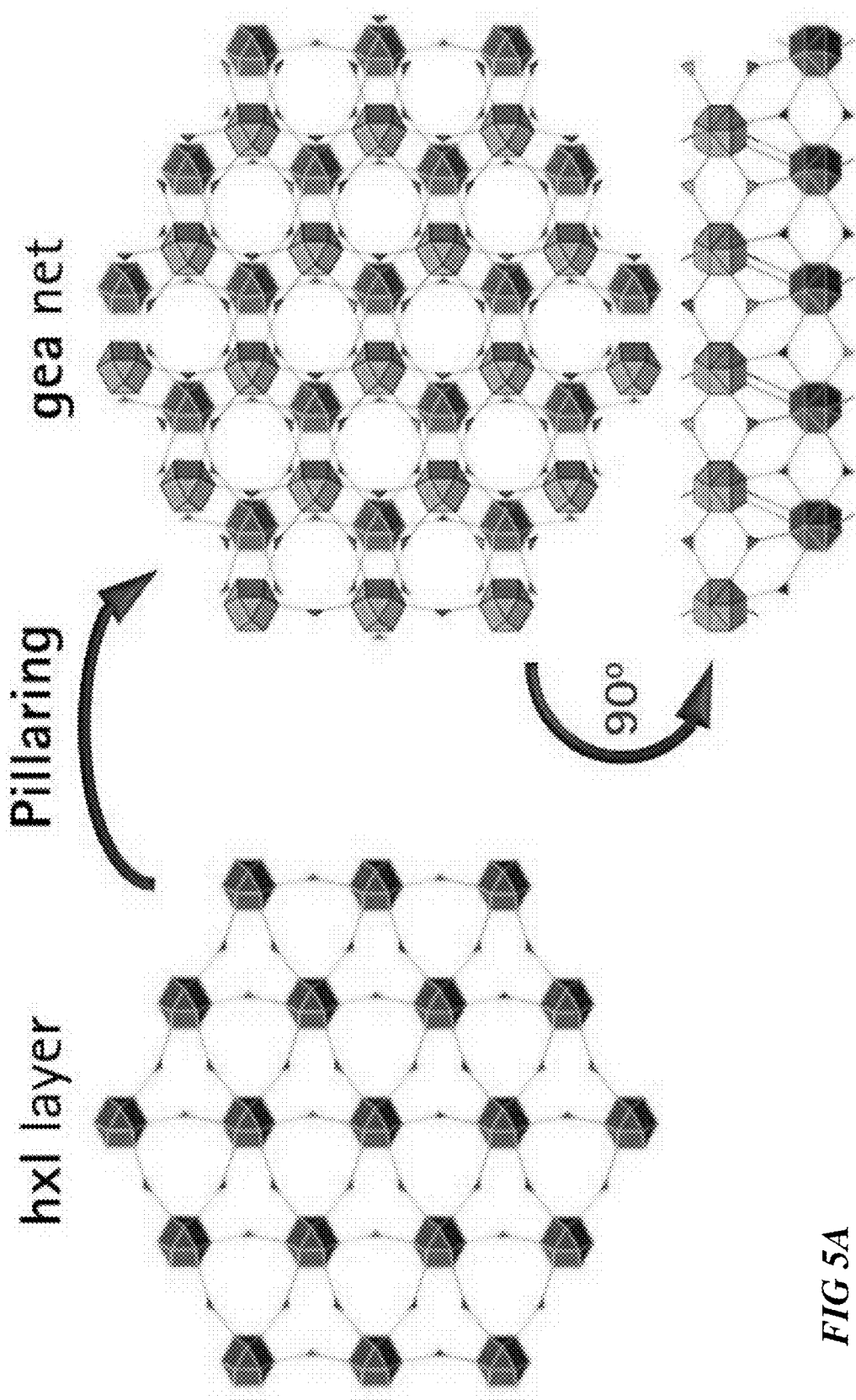

As shown in FIG. 5A-B, the resultant gea-MOF-1 reveals hexagonal close packing of the nonanuclear cluster MBBs and thus can be simplified as pillared hexagonal (hxl) layers. BTB ligands can serve as bridges between an MBB and its 6 neighboring MBBs in the plan to form the hxl layers, and simultaneously act as pillars between the neighboring layers, i.e. three on top and three on the bottom of each inorganic MBB that stands exactly in the right position to allow a hexagonal close packing.

Figure 7A:
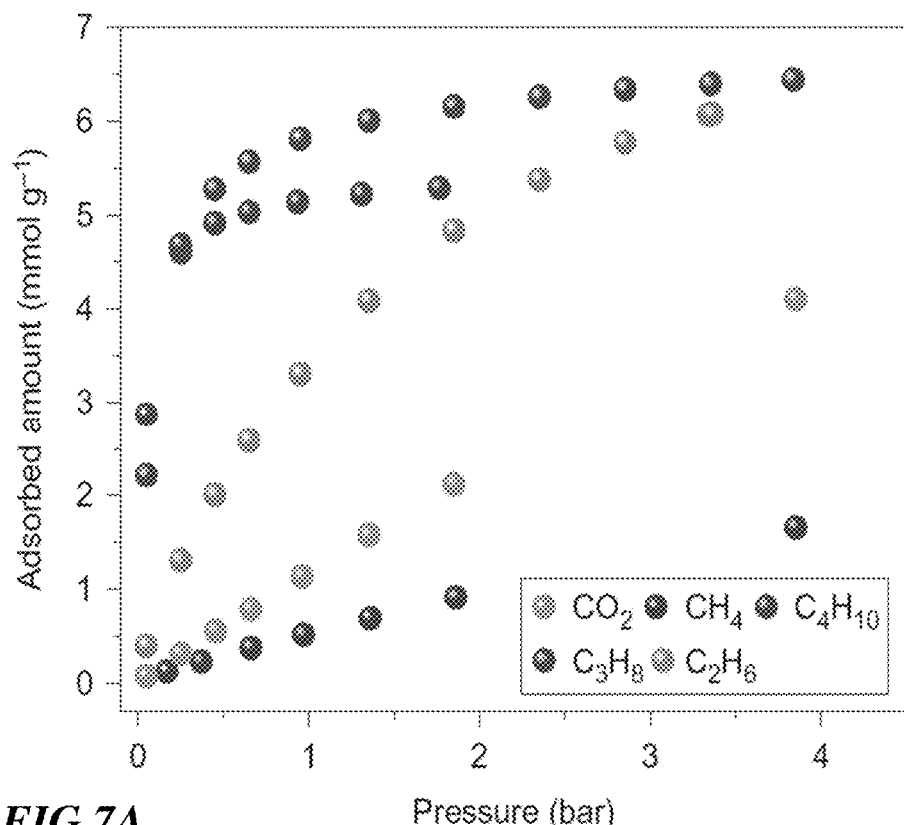
FIG. 7A illustrates the $CH_4$, $CO_2$, $C_2H_6$, $C_3H_8$ and n-$C_4H_{10}$ single gas adsorption isotherms at 298 K for gea-MOF-1, according to some embodiments.
Figure 7B:
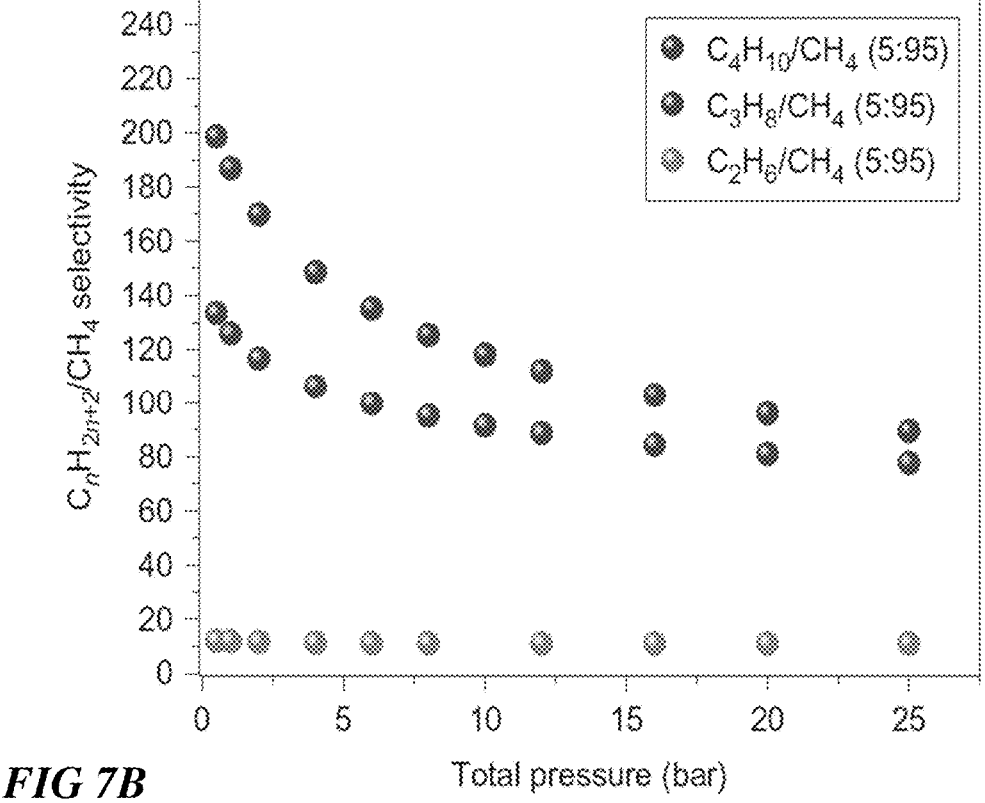
FIG. 7B illustrates predicted gea-MOF-1 selectivities in the adsorption of gas mixtures with molar ratios of $C_2H_6$/$CH_4$ (5:95), $C_3H_8$/$CH_4$ (5:95) and n-$C_4H_{10}$/$CH_4$ (5:95) using IAST calculations, according to some embodiments.

FIG. 6 shows a geometric representation of gea-MOF-1, gea-a net, and rht-a net topologies. The topology of gea-MOF-1 can be viewed as a more open variant of the ubiquitous (3,24)-connected rht net. The rhombicuboctahedron (24 vertices) from rht is substituted by the elongated triangular orthobicupola in gea-MOF-1 with only 18 vertices. The reduced points of extension lead to a related, but slightly different octahedral cavity. Their general shapes are similar, but only six faces of the octahedral cavity are capped, while the other two remain open. Moreover, the assembly of the MBBs in gea net leads to the hexagonal close packing (hcc), where the ones from rht are cubic close packed (fcc), and these differences lead to the formation of one-dimensional channels in gea-MOF-1. Further, the gea-MOF-1 exhibits three distinct cages (cavities A, B, and C) as shown in FIGS. 7A-C, respectively: cavity A, [3^12.8^6.12^2]: 22.4 Å×22.4 Å; cavity B, [3^8.4^3.8^9]: 24.8 Å×14.6 Å; cavity C [4^2.8^4]: 11.2 Å×5.6 Å; van der Walls (vdW) distances), the A cavities are aligned along [001] direction to form a channel (aperture: 12.8 Å×9,4 Å, vdW), whereas rht topology exhibits three cages exclusively, but no channel.

Investigation of Ar adsorption at 87 K showed that gea-MOF-1 exhibits a fully reversible Type-I isotherm, representative of a porous materials with permanent microporosity. The apparent BET and Langmuir surface areas, and pore volume were estimated to be 1490 $m^2 \cdot g^{-1}$, 1600 $m^2 \cdot g^{-1}$ and 0.58 $cm^3 \cdot g^{-1}$ respectively, which are in agreement with derived theoretical values. Further, the gea-MOF-1 maintains its optimal porosity up to temperatures of 360° C. under vacuum.

Examination of excess and absolute $CH_4$ and $CO_2$ gravimetric ($mmol \cdot g^{-1}$) and volumetric ($cm^3(STP) \cdot cm^{-3}$) uptakes at intermediates and high pressures showed that gea-MOF-1 adsorbs 40, 140 and 162 $cm^3(STP) \cdot cm^{-3}$ of $CH_4$ at 5, 35 and 50 bar, respectively. The resulting $CH_4$ working storage capacity, assuming 35 bar (following DOE standard) and 50 bar as the highest adsorption pressure and 5 bar as the lowest desorption pressure (following the requirement of the engine methane injection pressure), is ca. 100 and 122 $cm^3(STP) \cdot cm^{-3}$, respectively. Assuming the highest pressure limit at 35 bar, this volumetric working capacity, calculated assuming the density of gea-MOF-1 is constant and equivalent to the theoretical density, is similar to the corresponding working capacity reported for UiO-67(Zr), largely higher than UTSA-20 (ca. 80 $cm^3(STP) \cdot cm^{-3}$), but still lower than the working $CH_4$ storage capacity calculated for HKUST-1 and NU-125 (ca. 145 and 120 $cm^3(STP) \cdot cm^{-3}$). Assuming the highest pressure limit at 50 bar, the volumetric working capacities for NU-125 and HKUST-1 were found to be the highest (ca. 170 $cm^3(STP) \cdot cm^{-3}$).

In order to investigate the adsorption of larger and highly polarizable probe molecules, the adsorption of $C_2H_6$, $C_3H_8$ and n-$C_4H_{10}$ ($C_2$+) up to 4 bar was investigated on gea-MOF-1 and compared to $CO_2$ and $CH_4$ adsorption capabilities to estimate its potential use in the spectra of natural gas upgrading. The $CH_4$, $CO_2$, $C_2H_6$, $C_3H_8$ and n-$C_4H_{10}$ single gas adsorption isotherms at 298 K for gea-MOF-1 are shown in FIG. 7A. Based on the gradient of the isotherms at low pressure, the affinity of these molecules for gea-MOF-1 follows the sequence n-$C_4H_{10}$>$C_3H_8$>>$C_2H_6$>$CO_2$>$CH_4$. Despite the importance of hydrocarbon separation such as purification of $CH_4$ from condensable HC like ethane ($C_2H_6$), propane ($C_3H_8$) and butane (n-$C_4H_{10}$), few studies have focused on the selective adsorption of condensable hydrocarbons and were rarely debated. The $C_2$+ adsorption isotherms were much steeper at low pressure than $CH_4$, and also $CO_2$, indicative of the high affinity of gea-MOF-1 to $C_2$+.

FIG. 7B shows predicted selectivities in the adsorption of gas mixtures with molar ratios of $C_2H_6/CH_4$ (5:95), $C_3H_8/CH_4$ (5:95) and n-$C_4H_{10}/CH_4$ (5:95) using IAST calculations. Examination of single adsorption data using IAST confirmed the high selectivity of $C_2$+/$CH_4$, particularly for gas pair systems such as $C_3H_8/CH_4$ and n-$C_4H_{10}/CH_4$ (FIG. 26b). Therefore, gea-MOF-1 can be employed as a $C_3H_8/CH_4$ and n-$C_4H_{10}/CH_4$ separation agent for NG upgrading industry owing to its high affinity to $C_3H_8$ and n-$C_4H_{10}$ vs. $CH_4$ and $CO_2$.

The deliberate choice of the 3-connected triangular ligand was suggested by a comprehensive analysis of the RSCR database, revealing the absence of any enumerated minimal-edge transitive net for the assembly of 12-c cuo SBU and 3-c ligand (triangular SBU), suggesting the plausible incompatibility/mismatch of the aforementioned building units. The prompted discovery of the (3,18)-c net and the evident versatility of polynuclear RE carboxylate-based clusters expanded this approach, based on building units mismatch, to other polytopic ligands with the main aim to uncover new highly connected MOFs. Noticeably, careful examination of the resultant (3,18)-c net revealed the necessity to employ definite triangular organic building units, where the carbon of the carboxylate moieties as points of extension match the vertices of an equilateral triangle, in order to effectively space and arrange the 18-c MBBs in the requisite ABA hexagonal close-packing and subsequently construct the anticipated isoreticular gea-MOFs.

Presumably, distortion of the gea-a requisite symmetrical triangular building unit, i.e., expansion of the symmetrical triangular gea vertex figure in one direction via employing a relatively less symmetrical triangular organic building unit, where the carbon of the carboxylate moieties match the vertices of an isosceles triangle (two equal sides and two equal angles), will disrupt the ABA hexagonal close-packing necessary for the attainment of the pertinent (3,18)-c isoreticular gea-MOFs. Therefore, this will conceivably promote the adaptability of the resultant RE polynuclear carboxylate-based cluster to match the distinct imposed 3-connected ligand geometrical attributes and the subsequent construction of a cooperative highly connected REMOF. Indeed reaction conditions that formerly allowed the isolation of fcu-MOF, ftw-MOF and gea-MOF platforms, now, in the presence of less symmetrical 3-c ligands biphenyl-3,4,5-tricarboxylic acid (H3L1) and 9-(4-carboxyphenyl)-9Hcarbazole-3,6-dicarboxylic acid (H3L3), have permitted for the first time (i) the establishment a novel RE hexagonal prismatic SBU, a new 12-connected RE nonanuclear carboxylate-based cluster MBB and (ii) the formation of two highly connected MOF platforms, pek-MOF and aea-MOF, based on two newly revealed minimal edge-transitive nets, i.e., (3,8,12)-c net=pek topology and (3,12,12)-c net=aea topology.

Figures 8A, 8B:
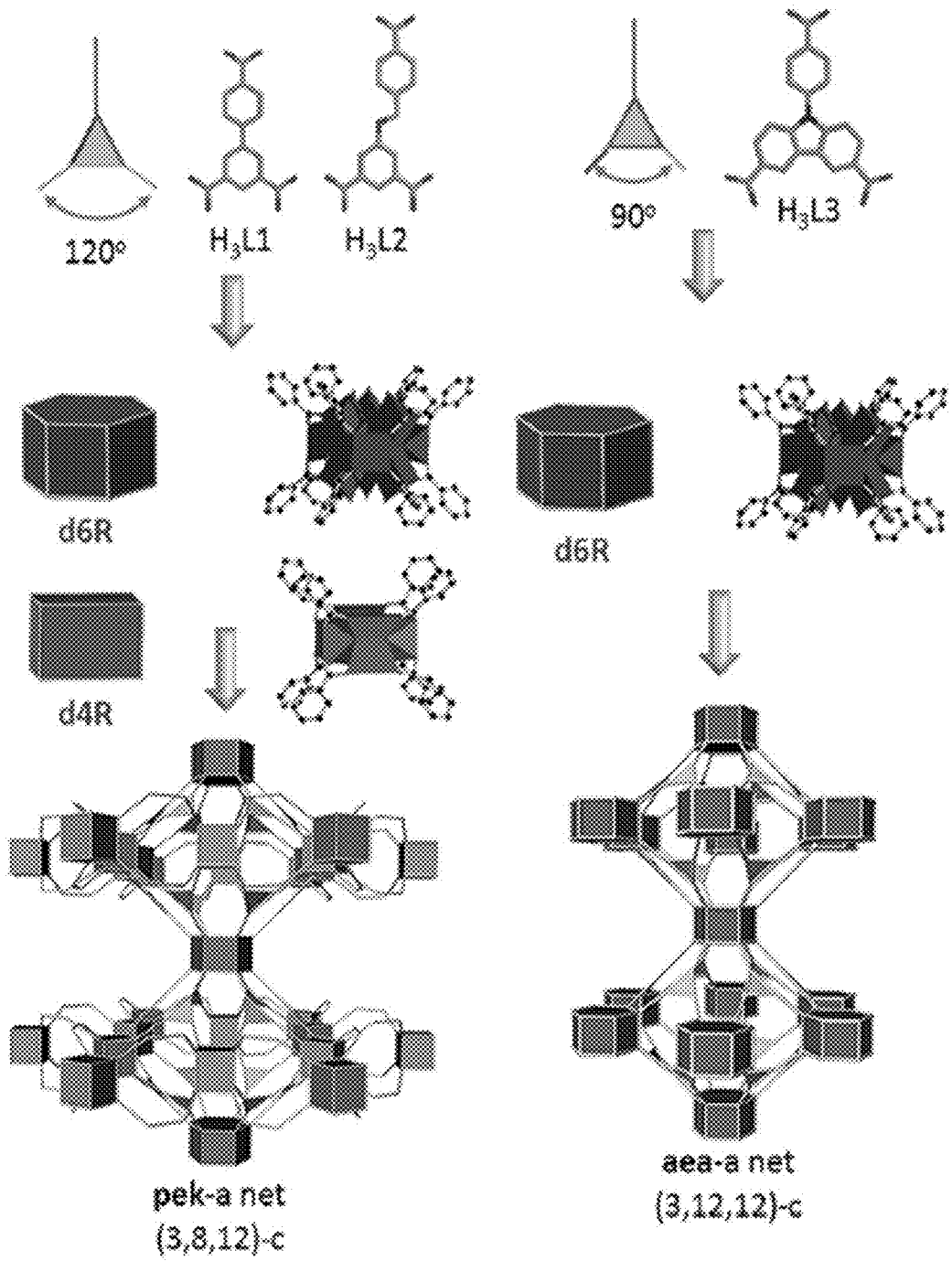
FIGS. 8A-B illustrate synthesis schematics for a pek-MOF and aea-MOF, respectively, according to some embodiments.
Figure 9A:
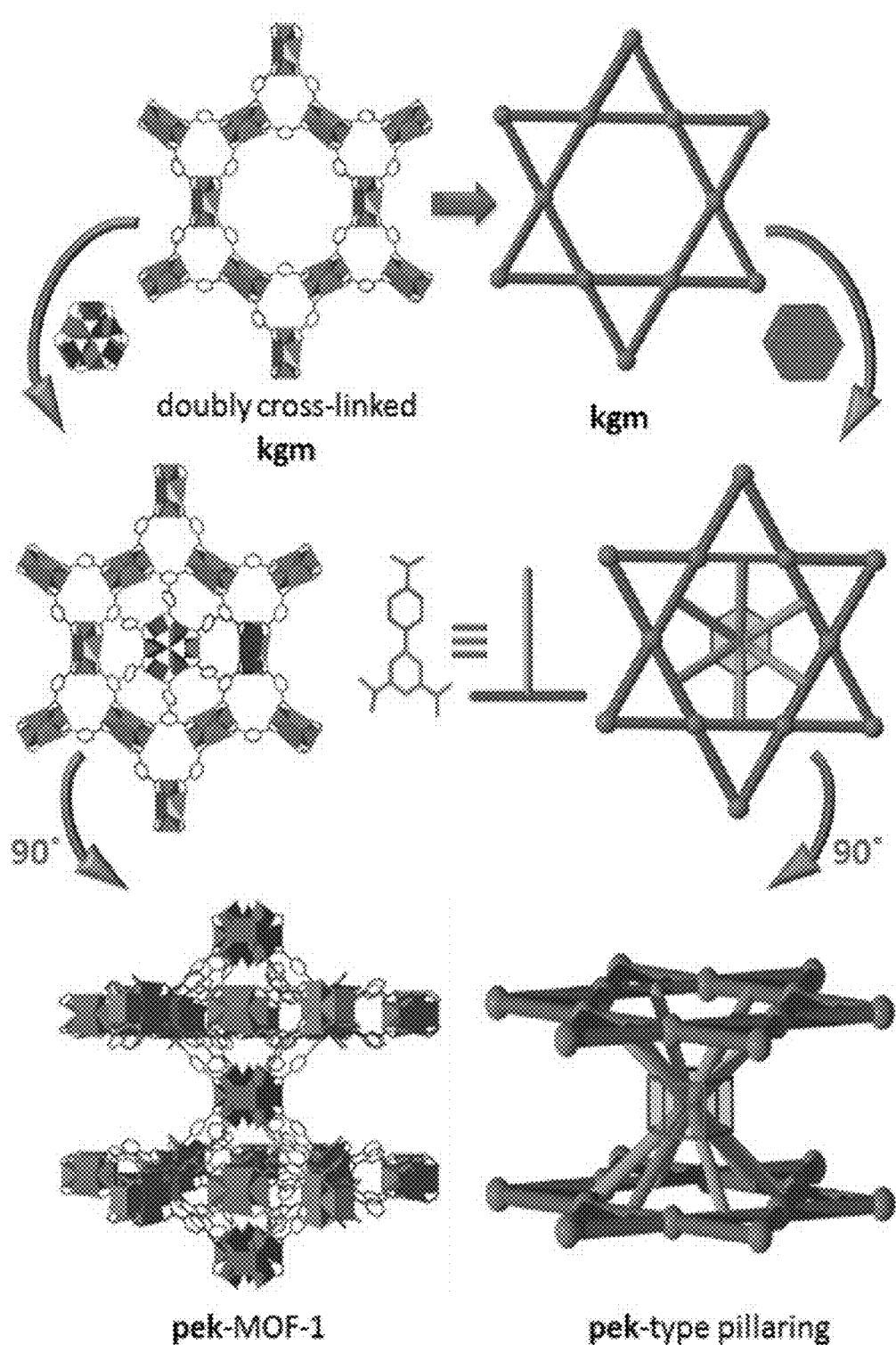
FIG. 9A illustrates a schematic showing the pek-type pillaring of the pek-MOF-1, according to some embodiments.
Figure 9B:
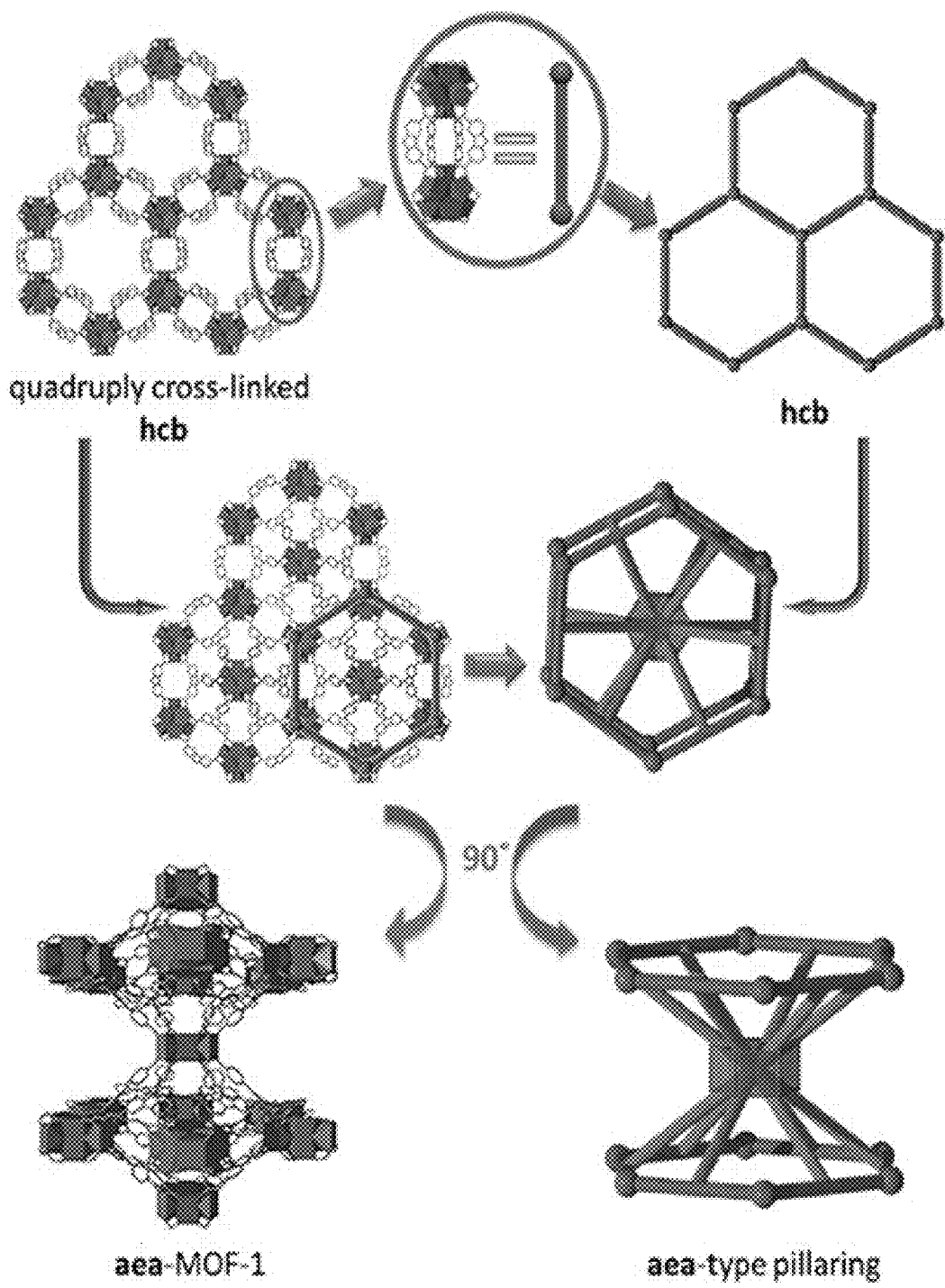
FIG. 9B illustrates a schematic showing the aea-type pillaring of the pek-MOF-1, according to some embodiments.

FIGS. 8A and 8B show synthesis schematics for a pek-MOF and a aea-MOF, respectively. Generally, the pek-MOF approach deviates from the gea-MOF-1 approach by reducing the symmetry of the ligand (e.g., H3L1 and H3L2) and reducing the length of the coordinating ligand moieties, while the aea-MOF approach deviates from the gea-MOF-1 approach by reducing the symmetry of the ligand (e.g., H3L3) and introducing different angles between the coordinating ligand moieties (i.e., the carboxylates). FIG. 9A is a schematic showing the pek-type pillaring of the pek-MOF-1. FIG. 9B is a schematic showing the aea-type pillaring of the pek-MOF-1.

Solvothermal reaction between $H_3L1$ and $Tb(NO_3)_3 \cdot 5H_2O$ in an N,N'-dimethylformamide (DMF)/water/chlorobenzene solution and in the presence of 2-FBA yielded transparent hexagonal crystals, formulated by single-crystal Xray diffraction (SCXRD), elemental microanalysis, NMR and water adsorption studies as follows: |(DMA)7|[(Tb9(μ3-OH)12(μ3-O)2(H2-O)9)(Tb6(μ3-OH)8 (2-FBzoate)2(HCO2)2(H2O)4.5)3(L1)12].(solv)x (1); (DMA=dimethylammonium cations, solv=solvent, L=C15H7O6, 2-fluorobenzoate (2-FBzoate)=C7H4FO2). The SCXRD study discloses that compound 1 crystallizes in a primitive hexagonal space group, P6/mmm. Analysis of the resultant crystal structure of 1 reveals the in situ formation of two highly connected and distinct terbium (Tb) polynuclear carboxylate-based clusters, namely an 8-c Tb hexanuclear cluster and a 12-c Tb nonanuclear cluster, and their subsequent copolymerization by the fully deprotonated tricarboxylate ligands (L) to yield a novel 3-periodic highly connected Tb-MOF. Analysis of the Tb hexanuclear cluster reveals that two Tb ions are each coordinated to nine oxygen atoms; namely, four carboxylates from four separate L1 ligands, four μ3-OHs and one terminal water molecule. The remaining four Tb ions are each coordinated to eight oxygen atoms; that is, four from carboxylates of four independent L1 ligands, and the other four coordination sites are completed by oxygen atoms from bridging μ3-OHs and disordered terminal ligands (i.e., 2-FBzoate, formate and water). Concisely, the resultant hexanuclear cluster, [$Tb_6(μ_3$-OH$)_8$ ($O_2$C—$)_8$($O_2$C—$C_6H_4$F$)_2$($O_2$C—H$)_2$($H_2$O$)_{4.5}$], is capped by 8 carboxylates from 8 different L1 ligands (FIG. 8A) and 4 carboxylates from four terminal ligands (evenly 2-FBzoate and formate anions) to give an 8-connected MBB, [$Tb_6(μ_3$-OH$)_8$($O_2$C—$)_8$], with points of extension corresponding to carbons of the carboxylate moieties from eight distinct tricarboxylate ligands and matching the d4R vertex figure of a fully symmetrical 8-connected node. Similarly, inspection of the Tb nonanuclear cluster unveils that six Tb ions are coordinated to eight oxygen atoms (that is, two from carboxylates of two separate L1 ligands, four μ3-OH, two μ3-O and one from a terminal water molecule), and that the remaining three Tb ions are coordinated each to nine oxygen atoms (namely, four from carboxylates of four separate L1 ligands, four μ3-OH and one from a terminal water molecule). Distinctly, the nonanuclear cluster, [$Tb_6(μ_3$-OH$)_8(μ_3$-O$)_2$($O_2$C—$)_{12}$($H_2$O$)_9$], is capped by 12 carboxylates from 12 different L1 ligands (FIG. 8A) to give a new 12-connected MBB, [Tb9 (μ3-OH$)_{12}$(μ3-O$)_2$(O2C—)12], with points of extension corresponding to carbons of the carboxylate moieties from 12 distinct tricarboxylate ligands and providing the hexagonal prism arrangement, matching the d6R vertex figure of a 12-connected node with a 6-fold symmetry. Appreciably, the combination of the aforementioned 12-c MBB, [Tb9 (μ3-OH)12(μ3-O)$_2$(O2C—)$_{12}$], and 8-c MBB, [Tb6(μ3-OH)$_8$(O$_2$C—)$_8$], with the 3-c tricarboxylate ligand resulted in the formation of an unprecedented highly connected Tb-MOF with a (3,8,12)-connected net and pek underlying topology, Tb-pek-MOF-1 (FIG. 8A). It is worth noting that the newly explored trinodal pek net has the transitivity [3244], a minimal edge transitive net with only two edges. Appropriately, pek net can categorized as a suitable blueprint for the design of MOFs. Markedly, the projected versatility of RE polynuclear clusters has permitted the isolation and introduction of two key highly connected MBBs, namely the d4R SBU and most decisively the d6R SBU, looked-for in MOF crystal chemistry and deemed appropriate for the effective practice of reticular chemistry. The recent study on highly connected RE-MOFs postulated the plausible relationship between the 12-connected RE hexanuclear and the 18-connected RE nonanuclear clusters observed in fcu-MOFs7h and in the gea-MOF-1,5c respectively. Observably, the triangular ligand geometrical attributes and subsequent net incompatibility have prompted the incorporation of three additional RE metal ions in the hexanuclear 12-c MBB (cuo) to afford the accommodation of six additional peripheral carboxylate moieties from the 3-c bridging ligands, thus resulting in the perceived cluster evolution to a nonanuclear 18-c MBB (eto) (FIG. 8A). The Tb-pek-MOF-1 discloses another intriguing facet enriching the adaptability of the RE polynuclear clusters. Namely, the attainment of the first (3,8,12)-c RE-MOF, the pek-MOF-1, illustrates the attractive prospective to reduce the points of extension (n-connectivity) in the parent RE hexanuclear (cuo) and the RE nonanuclear clusters (eto). Specifically, in the hexanuclear cluster four of the 12 carboxylate moieties from the bridging ligands, originally connecting and acting as points of extension in the fcu-MOFs, are substituted by carboxylates from terminal ligands (2-FBzoate and formate anions), thus affording the remaining eight connecting carboxylates' arrangement in a cube-like fashion, d4R. The d4R building unit, commonly occurring in conventional inorganic zeolites, was employed effectively to target and construct zeolite-like MOFs (ZMOFs). In the pek-MOF-1 nonanuclear cluster all the 12 coordinating carboxylate moieties, capping the cluster and arranged in an hexagonal prism fashion (d6R), belong solely to the 3-connected bridging ligands and thus suggesting the plausible occurrence of the nonanuclear cluster and its rearrangement to accommodate only 12 coordinating carboxylates, in contrast to nonanuclear 18-c MBB observed in the gea-MOF-1 where the 18 coordinating carboxylate moieties capping the polynuclear cluster are from bridging ligands. The isolation of the pek-MOF-1 has permitted the enclosure of two additional RE-MBBs (d4R and d6R SBUs) in the repertoire of highly connected RE-MBBs. Based on the open literature search and the Cambridge Structural Database (CSD) analysis, the aforementioned hexagonal prism building unit (d6R) has never been observed in MOFs as a nonanuclear carboxylate-based cluster. However, a zirconium hexanuclear carboxylate-based cluster was reported to act as a d6R SBU to form a shp-MOF when combined with a square-like tetratopic carboxylate ligand. It is worth noting that variation of the hexanuclear cluster's connectivity has been recently studied with zirconium MOFs but so far was not observed with RE hexa-/nonanuclear clusters. As customary in RE chemistry, isolated reaction conditions for a given RE ion can be extrapolated effectively to other RE metals and subsequently construct related isostructural REMOFs. Indeed, reactions between Y(NO$_3$)$_3$.6H$_2$O and fluor, under similar reaction condition to 1, resulted in the analogous Yttrium based pek-MOF-1 (2), formulated by SCXRD as |(DMA)$_7$|[(Y$_9$ (μ$_3$-OH)$_{12}$(μ3-O)$_2$(H$_2$O)$_9$)(Y$_6$(μ$_3$-OH)8(2-FBzoate)2 (HCO$_2$)$_2$(DMF)$_{0.67}$(H$_2$O)$_4$)$_3$(L1)$_{12}$].(solv)x (2); (DMA=dimethylammonium cations, solv=solvent, L1=C$_{15}$H$_7$O$_6$, 2-FBzoate=C$_7$H$_4$FO$_2$, DMF=C$_3$H$_7$NO). The purity of compounds 1 and 2 was confirmed by similarities between the experimental and calculated powder Xray diffraction (PXRD) patterns. Additionally, both compounds show favorable water and thermal stability, important attributes for the exploration of their associated porous system in relevant applications. The pek-MOF-1 structure encloses cavities with a truncated hexagonal pyramidal-like contour and having diameters of 13.8 Å (height) and 9.8 Å (width) (in case of 1), and accessible via two different apertures 4.9 and 7.6 Å. The said cage is derived from the hexagonal arrangement, in the equatorial plan, of six hexanuclear clusters and the capping by two nonanuclear clusters, in the two axial positions. Moreover, the structure has three intersecting infinite square channels with a kagome like motif and having an estimated diameter of 14.5 Å, taking van der Waals (vdW) radius into consideration. The corresponding solvent accessible free volumes for 1 and 2 were estimated to be 58.6 and 59.4%, respectively, by summing voxels more than 1.2 Å away from the framework using PLATON software. Further structural analysis of the pek-MOF-1, revealed that each hexanuclear cluster is surrounded by four neighboring hexanuclear clusters to afford their subsequent arrangement in a 2-periodic sheet reminiscent of a kagome layer. The resultant kagome-like layers are further intercalated by a periodic array of nonanuclear clusters arranged in a hexagonal layer manner where each nonanuclear cluster superimposes with the two adjacent kagome hexagonal rings (FIG. 9A). Correspondingly, the pek-MOF structure can be regarded as built from pillared layers. Specifically, when considering only the isophthalate moiety of the 3-c ligand, the structure now represents a regular AAA stacking of layers, made from 8-c hexanuclear clusters, bridged to four neighboring ones through two isophthalate ligands each time, and representing a well-known kagome (kgm) pattern (FIG. 9A). This can be related to the ubiquitous copper isophthalate sql and kgm layers found in many MOFs,2,6,18 but in this case with a doubled connectivity of the MBBs (8 for the RE hexanuclear versus 4 for the Cu paddle wheel) resulting in doubly cross-linked kgm layers. The resultant doubly cross-linked kgm layers are then pillared on top and bottom direction by the 12-c MBB, d6R, to form the overall (3,8,12)-c pek net. At this stage, the analogy can be made with two related nets based on the pillaring of simple kgm layers by 6-c nodes, agw19 and eef,2 where the vertex figures of the 6-c nodes match those from a trigonal prism and an octahedron, respectively. Unsurprisingly, the superimposition of agw or eef net with its corresponding mirror image net leads to the attainment of the pek net. Credibly, the two 3-periodic nets (agw and eef) based on pillared 2-periodic kgm are regarded as suitable targets and ideal blueprints for the practice of the SBL approach toward directed assembly of MOFs. Similarly, the pek net suggests the great potential to extend the SBL approach to doubly cross-linked layers in general and to the doubly cross-linked kgm layer in particular. In order to affirm the advocated SBL approach based on the doubly cross-linked kgm layer and associated pek topology, a suitable expanded ligand was designed and synthesized, 3-c tricarboxylate ligand, namely the 5-(4-carboxybenzyloxy)-isophthalic acid (H$_3$L2). In contrast to the original ligand, H$_3$L1, the isophthalate moiety believably responsible for the formation of the doubly cross-linked kgm layer is maintained while the 5-position of the isophthalate moiety is functionalized, providing a further elongated 3-c ligand than H$_3$L1 (FIG. 8A). As anticipated, reactions of H$_3$L2 with Tb or Y nitrate salts, under similar conditions as pek-MOF-1, afforded colorless hexagonal crystals formulated by SCXRD studies as |(DMA)$_7$|[(Tb$_9$(μ$_3$-OH)$_{12}$(μ$_3$-O)$_2$(H2O)$_9$)(Tb$_6$(μ$_3$-OH)$_8$(2-FBzoate)$_2$(HCO$_2$)$_2$(H$_2$O)$_3$)3(L2)12].(solv)x (3) and |(DMA)$_7$|[(Y$_9$(μ$_3$-OH)$_{12}$(μ$_3$-O)$_2$(H$_2$O)$_9$)(Y$_6$(μ$_3$-OH)$_8$(2-FBzoate)$_2$(HCO$_2$)$_2$(DMF)$_{1.66}$(H$_2$O)$_3$)$_3$(L2)$_{12}$].(solv)x (4), respectively (L2=C$_{16}$H$_9$O$_7$, 2-FBzoate=C$_7$H$_4$FO$_2$). As envisioned, compounds 3 and 4 are isoreticular analogues of pek-MOF-1, named pek-MOF-2, constructed from the identical double kgm layers but at present connected together through elongated pillars, resulting in an increased spacing between the layers along the c-axis as evident by the observed increase in the c parameter (21.1 Å versus 26.4 Å in pek-MOF-1 and pek-MOF-2, respectively).

The association of the pek-MOF structure with the kgm layer prompted exploration of other 3-c ligands that might disturb the formation of the requisite kgm layer and prospectively, once again, promote the effect of the ligand geometrical attributes on the resulting topology. It was opted to explore the carbazole-based ligands due to their associated contracted angle between the two carboxylate moieties, namely a 90° angle as compared to 120° in the isophthalate moiety. Accordingly, the 9-(4-carboxyphenyl)-9H-carbazole-3,6-dicarboxylic acid (H$_3$L$_3$) tricarboxylate ligand, which has 90° angle between carboxylate groups on the carbazole moiety, was designed and synthesized (FIG. 8B). Indeed, reactions of H$_3$L3 with Y(NO$_3$)$_3$.6H$_2$O, in the presence of the cluster directing agent 2-FBA, resulted in the formation of colorless hexagonal crystals, characterized and formulated by SCXRD and elemental microanalysis studies as |(DMA)$_{1.3}$(Y$_9$(μ$_3$-OH)$_{12}$(μ$_3$-O)$_2$(Y$_{1.2}$)(H$_2$O)$_9$(2-FBzoate)$_{12}$)$_{0.33}$|[Y$_9$(Y$_{0.28}$)(μ3-OH)$_{12}$(μ$_3$-O)$_2$(H2O)$_9$(Y$_9$(μ$_3$-OH)$_{12}$(μ$_3$-O)$_2$(H$_2$O)$_9$)$_2$(L3)$_{12}$].(solv)x (5) (L3=C$_{15}$H$_7$O$_6$, 2-FBzoate=C$_7$H$_4$FO$_2$). The SCXRD study discloses that compound 5 crystallizes in a primitive hexagonal space group P6/mmm. Analysis of the resultant crystal structure of 5 reveals the formation of a novel 3-periodic highly connected Y-MOF based solely on nonanuclear Y carboxylate-based clusters, formed in situ, and similar to the 12-c nonanuclear RE cluster observed in the pek-MOF. Specifically, the structure encloses three crystallographically independent nonanuclear clusters, each built by nine yttrium (Y) ions and capped by 12 carboxylate moieties, but only two of the nonanuclear clusters are copolymerized by the fully deprotonated tricarboxylate ligands (L3) to form a 3-periodic MOF hosting the third discrete nonanuclear cluster, capped by 12 carboxylate moieties from terminal 2-fluorobenzoate ligands, in its porous system. From a topological analysis perspective, the two nonanuclear clusters, 12-connected MBBs, have the same d6R vertex figure as observed in the pek-MOF, but are topologically distinct and thus their assembly with the 3-c ligand reveals the discovery of a novel highly connected Y-MOF with a trinodal (3,12,12)-c net and aea underlying topology, Y-aea-MOF-1 (FIG. 8B). Analogous to the pek net, the new trinodal aea net is a minimal edge transitive net, transitivity [3244], and is an appropriate target for MOF crystal chemistry. The purity of compounds 5 was confirmed by similarities between the experimental and calculated PXRD patterns. The aea-MOF-1 structure encloses a rhombic-like cage with estimated diameters of 9.2-13.7 Å (height) and 14.8 Å (width), taking vdW radius into consideration, having two separate apertures with relative dimensions of 5.2×3.5 Å and 10×5.4 Å. In addition, the structure possesses three intersecting infinite square channels with an estimated diameter of 12.5 Å. The corresponding solvent accessible free volume for 5 was estimated to be 55%, by summing voxels more than 1.2 Å away from the framework using PLATON software. Similar to the pek-MOF, the structure of aea-MOF-1 can be deconstructed into 2-periodic layers pillared by 12-c nonanuclear clusters. The layers are composed of one kind of nonanuclear clusters where each nonanuclear cluster is surrounded by three neighboring nonanuclear clusters, and linked in the plane, to afford their subsequent arrangement in a 2-periodic sheet reminiscent of a honeycomb (hcb) lattice. The resultant hcb layers are further intercalated by a periodic array of the second and distinct nonanuclear clusters arranged in a hexagonal layer manner where each nonanuclear cluster regarded as built from pillared layers. Specifically, when considering only the carbazole dicarboxylate part of the 3-c ligand (i.e., discounting the connectivity via the benzoate moieties), it is possible to isolate some bidimensional layers, where each nonanuclear cluster is quadruply connected to each of three neighboring others via four carbazole dicarboxylate moieties (FIG. 9B). Topological simplification of the resultant 2-periodic arrangement reveals the occurrence of an hcb layer, considered in this case as a quadruply cross-linked hcb. It is envisioned that the newly discovered (3,12,12)-c aea net and the quadruply cross-linked hcb layer are promising blueprints for the directed assembly of highly connected and pillared MOFs using the SBL approach.

Figure 10:
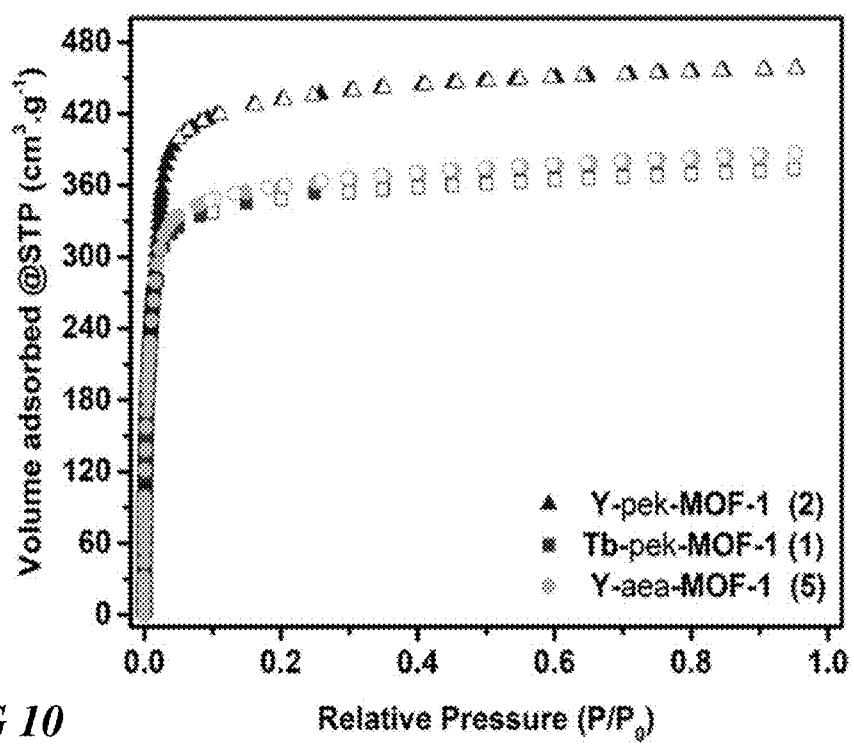
FIG. 10 illustrates an Ar adsorption isotherm recorded at 87 K showing that Y and Tb analogues of pek-MOF-1 exhibit fully reversible Type-I isotherm, according to some embodiments.
Figure 11A:
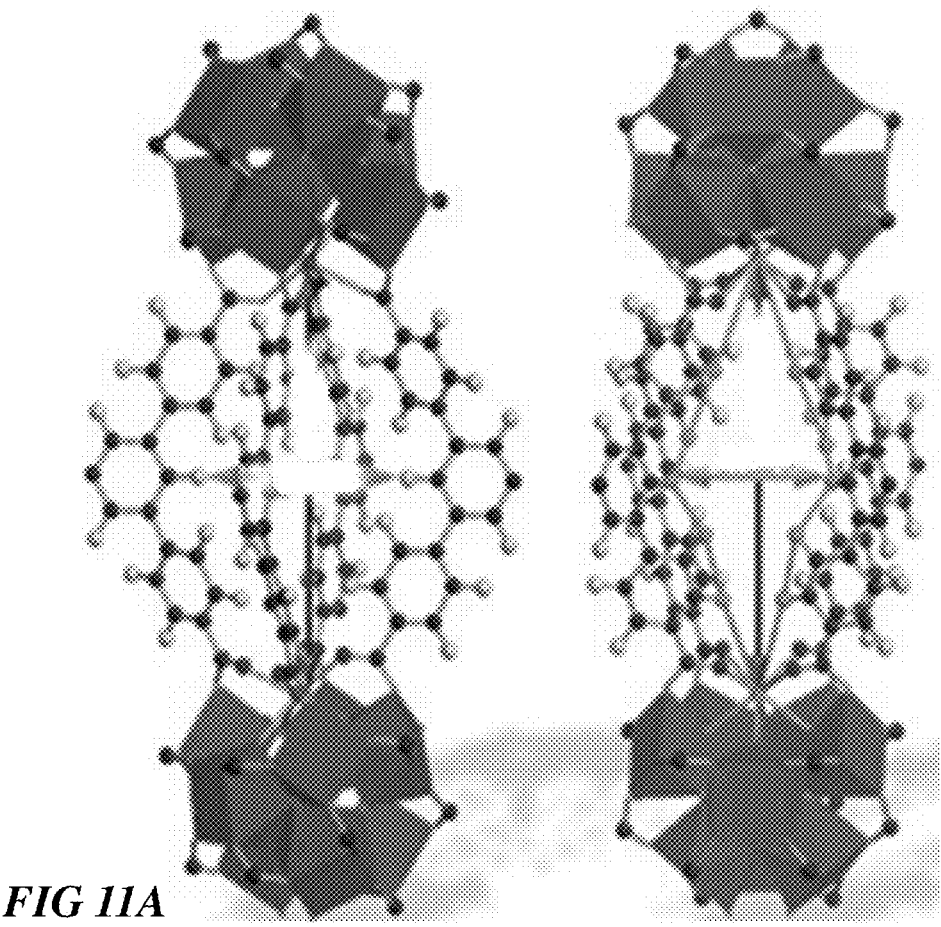
FIGS. 11A-C illustrates the three cages of a gea-MOF-1, according to some embodiments.
Figure 11B:
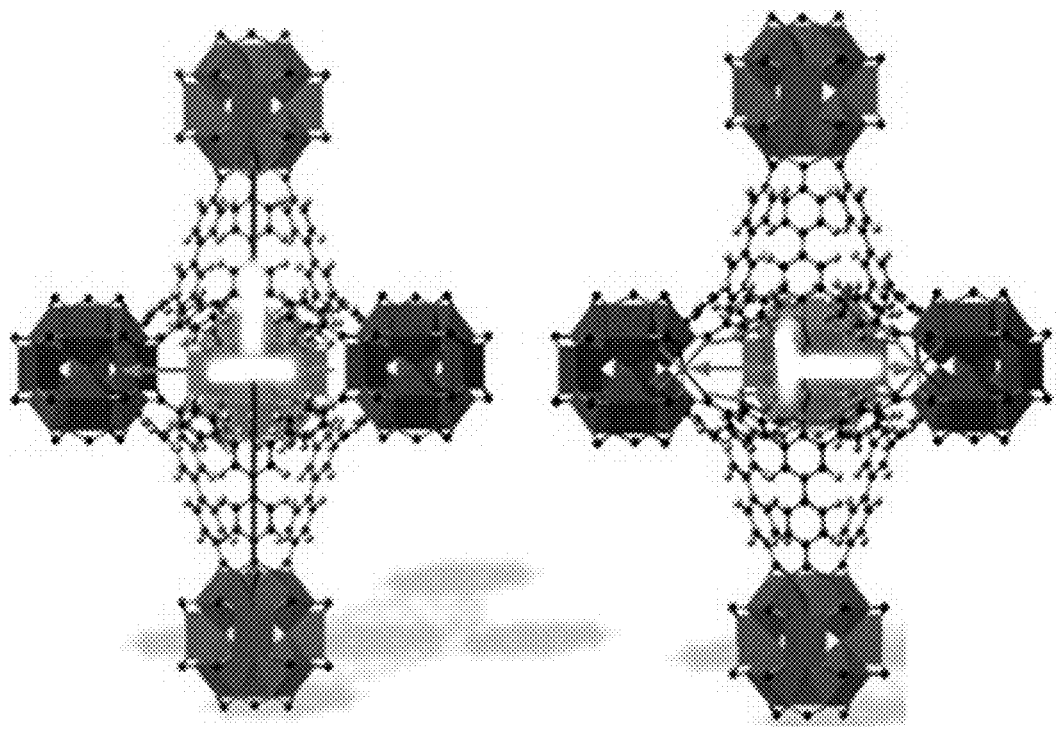
Figure 11C:
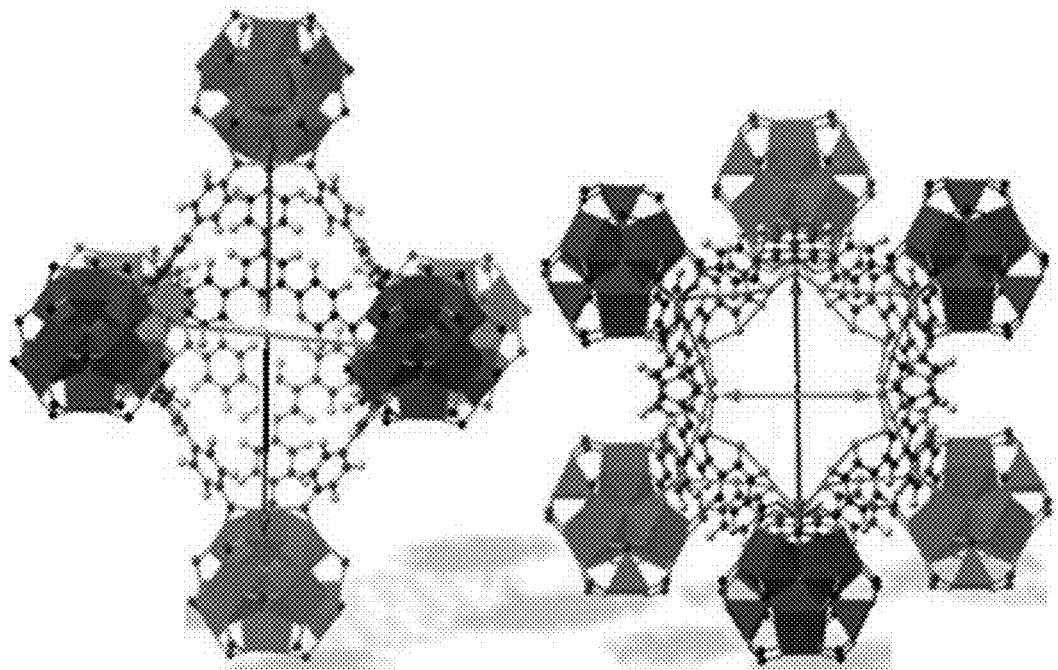

The Ar adsorption isotherm recorded at 87 K showed that Y and Tb analogues of pek-MOF-1 exhibit fully reversible Type-I isotherm, as shown in FIG. 10, indicative of a porous material with permanent microporosity. The apparent BET surface area and associated total pore volume were estimated to be 1330 m2 g-land 0.47 cm3 g-1 for the pek-Y analogue, and 1608 m2 g-1 and 0.58 cm3 g-1 for the pek-Tb analogue. The experimentally obtained total pore volumes are in excellent agreement with the associated theoretical values derived from SCXRD data, i.e., 0.47 cm3 g-1 for 1 and 0.58 cm3 g-1 for 2. The pore size distribution (PSD) for the pek-Y analogue was determined using the Ar adsorption data and revealed two type of pores with average sizes centered around 10 Å (cage) and 16.8 Å (channels). Akin porosity study based on Ar adsorption was performed on the Y-aea-MOF-1 analogue, as shown in FIG. 10, and presented an apparent BET surface area and a total pore volume of 1435 m2 g-1 and 0.49 cm3 g-1, respectively.

The resultant gea-MOF-1 can be based on the augmented gea net, a new (3,18) connected topology with [2244] net transitivity (2 type of nodes, 2 kind of edges, 4 kind of faces and 4 kind of tiles). Coordination sequence for each node of the gea net: a) 18 12 132 44 378 96 744 170 1242 264, TD10=3101; b) 3 44 22 214 63 514 124 934 207 1486, TD10=3612. The newly disclosed highly-connected binodal gea net, encompassing only two kind of edges and not self-dual, can be an ideal blueprint for MOF crystal chemistry and especially the deliberate construction of MOFs based on the SBB approach.

The SBB approach can be founded on the deliberate employment of a given metal-organic polyhedral (MOP) as a means to facilitate the access and generation of a desired highly connected building block. Accordingly, the (3,18)-c can be introduced as an ideal blueprint for deliberate (predicted and anticipated gea-MOFs) construction of gea-MOFs based on the assembly of MOPs as 18-connected SBBs, building block substitution/decoration (e.g. cluster vs. MOP), without concern for interpenetration, not self-dual.

One requirement to translate the gea-a blueprint net into practice for MOF chemistry can be to elect and construct a MOP acting as an 18-connected SBB, where its points of extension coincide with the geometrical building unit corresponding to the augmentation of the 18-connected vertex (i.e., vertex figure) of the given gea net.

A 12 copper paddlewheels [$Cu_2(O_2CR)_4$] joined by 24 isophthalate (1,3-BDC) can be used as an SBB for the construction of rht-MOFs. The eto polyhedron can construct the associated 18-connected MOP based on nine 4-connected MBB joined by twelve ligands with 120O angle and six ligands with 90O angle. Accordingly, a survey of the CSD data base and open literature revealed the existence of such an eto MOP based on nine copper paddlewheels [$Cu_2(O_2CR)_4$] bridged by twelve 4,4'-(pyridine-2,6-diyl)dibenzoic acids with 120O angle and six carbazole-3,6-dicarboxylic acids with 90° angle. In this MOP, the bent position of each of these 18 ligands lies perfectly on the vertices of the desired eto SBB. Further geometrical analysis of the gea-a net reveals that transposition of such an SBB into the anticipated gea-MOF platform requires the employment of a trefoil-like ligand encompassing two branches containing 120° angle dicarboxylic acid extremities and a third branch with a 90° angle dicarboxylic acid extremity (Scheme 1).

A trefoil-like ligand can be designed to contain the required geometrical information and Multisteps can be used to synthesize 5',5''''-((5-((4-(3,6-dicarboxy-9H-carbazol-9-yl)phenyl)ethynyl)-1,3-phenylene)bis(ethyne-2,1-diyl))bis([1,1':3',1''-terphenyl]-4,4''-dicarboxylic acid), referred to as $H_6L$ and depicted in Scheme 1 (see SI for detailed synthesis).

Scheme 1. Ligand used for the synthesis of gea-MOF-2, containing two dicarboxylic acid moieties with 120° angles and one with 90° angle.

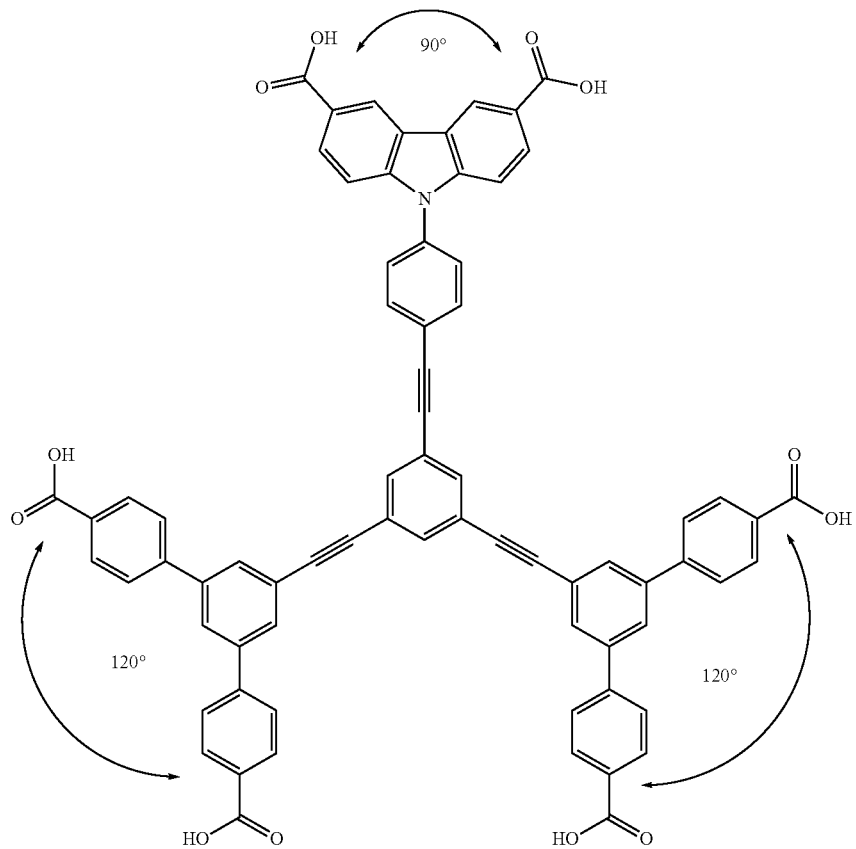

Reaction of the designed ligand with copper cations can yield a very low density gea-MOF (calc. density≈0.29 g·cm, free volume 85% for solvent free structure), gea-MOF-2, exhibiting the anticipated (3,18)-connected topology (considering the 18-connected MOP as a node for the topological analysis). The design and synthesis of this MOF would have been impossible to unveil previously, as its complex gea topology was not reported.

MOFs can be rationally designed. The gea-MOFs reported here is an example where a previously unknown topology can be discovered in a specific system (i.e., $RE^{III}$-tricarboxylate), and successfully transposed to a different chemical system ($Cu^{II}$-hexacarboxylate). Careful selection of the needed SBB and the distinctiveness of the SBB approach for the deliberate construction of MOFs can be important. Edge transitive nets are not the only suitable targets in crystal chemistry and that highly-connected binodal nets with two kinds of edges (minimal transitivity, i.e minimum numbers of kinds of vertices and edges) can also be proper targets when using the SBB approach which permits the attainment of the required and necessary directional and geometrical information in the same SBB.

Figure 12:
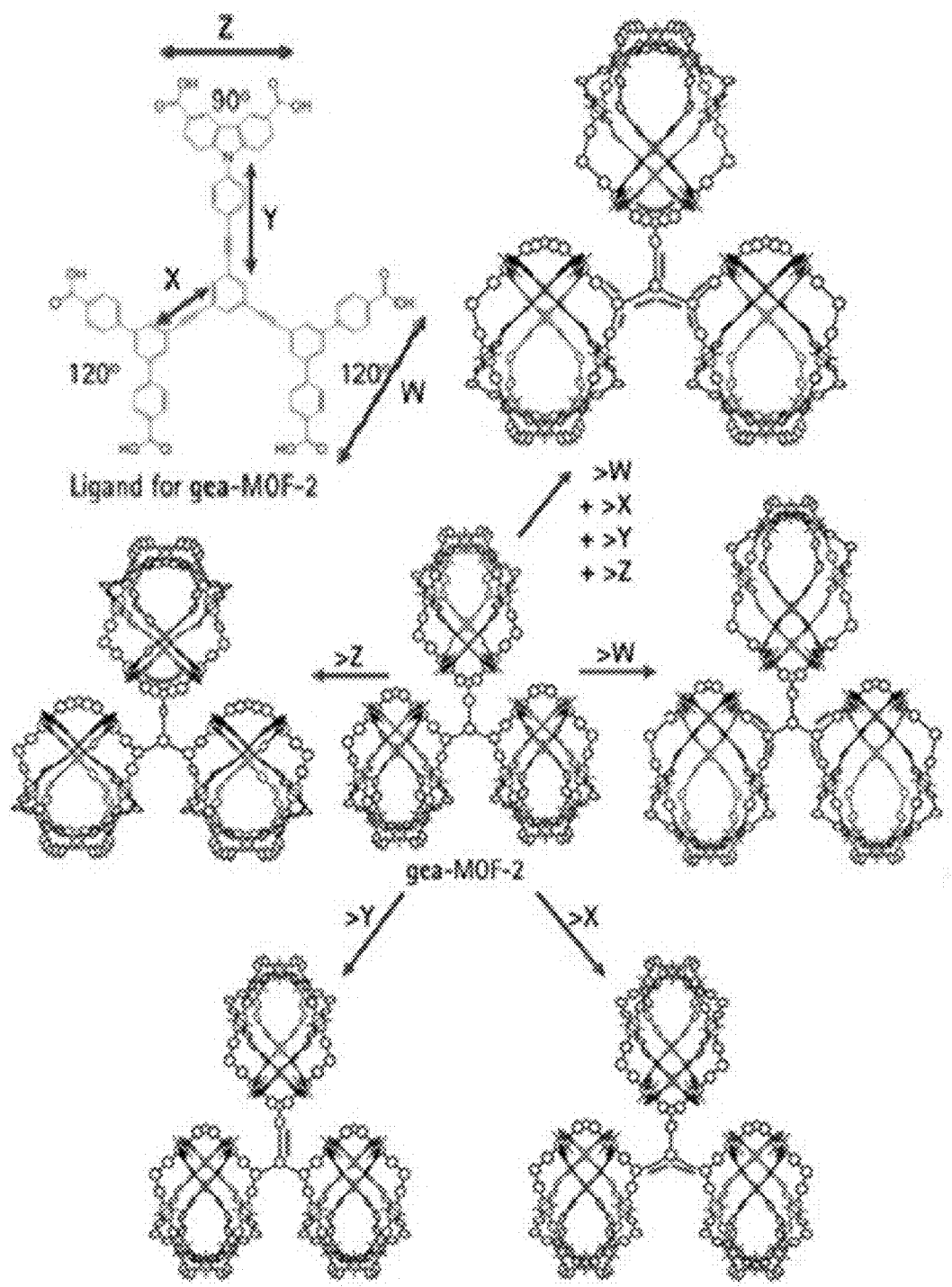
FIG. 12 illustrates tuning potential for a gea-MOF-2, according to some embodiments.

Geometrical analysis shown in FIG. 12 suggests that the resultant gea-MOF platform is amenable, par excellence, to expansion (without concern for interpenetration) via four independent parameters (W, X, Y, Z), allowing in fine a higher degree of tunability than in rht-MOFs (so far only 2 independent expansion parameters have been reported).

Figure 13A:
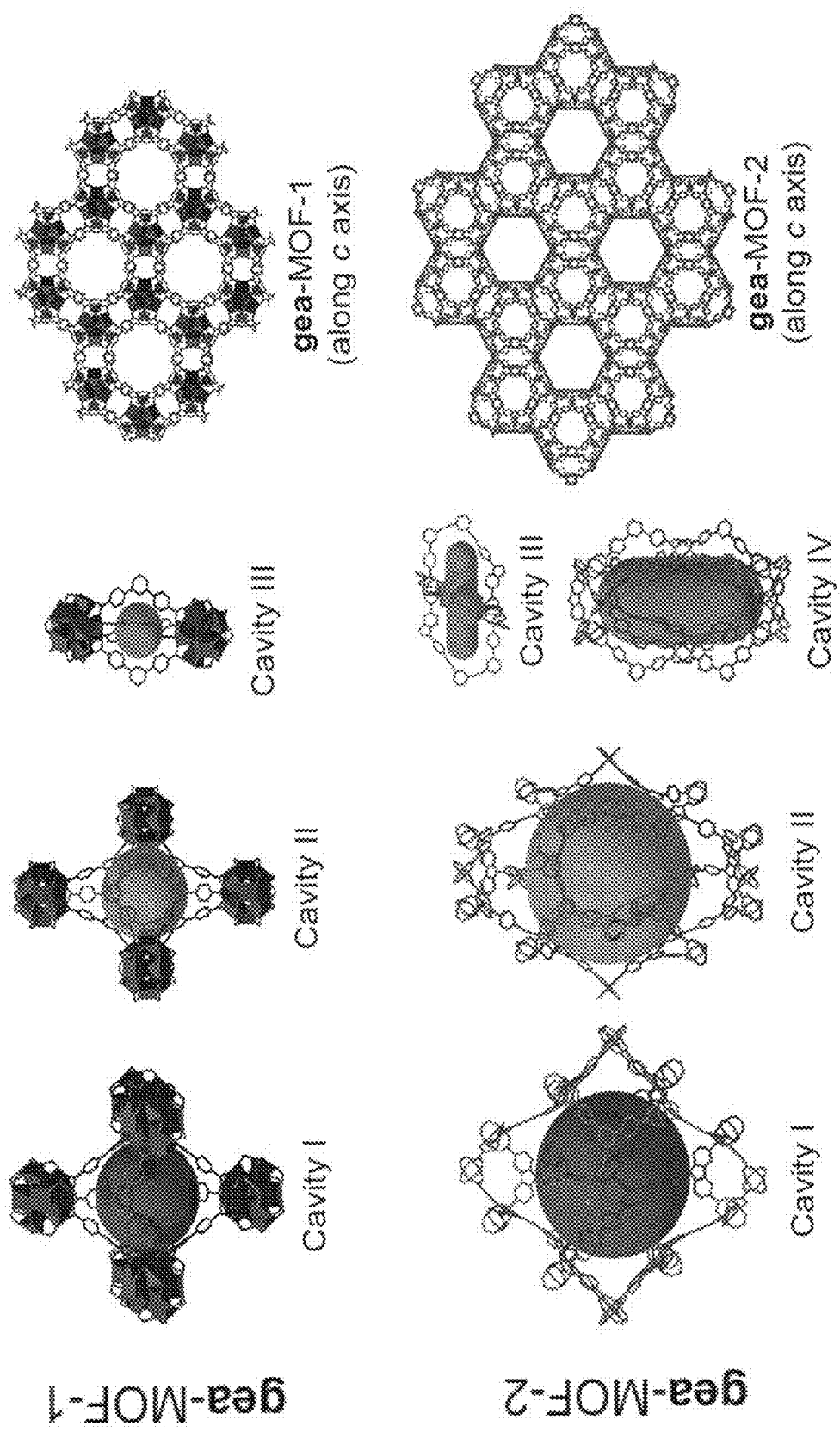
FIGS. 13A-B illustrate the structures of gea-MOF-1 and gea-MOF-2 topologies, according to some embodiments.
Figure 13B:
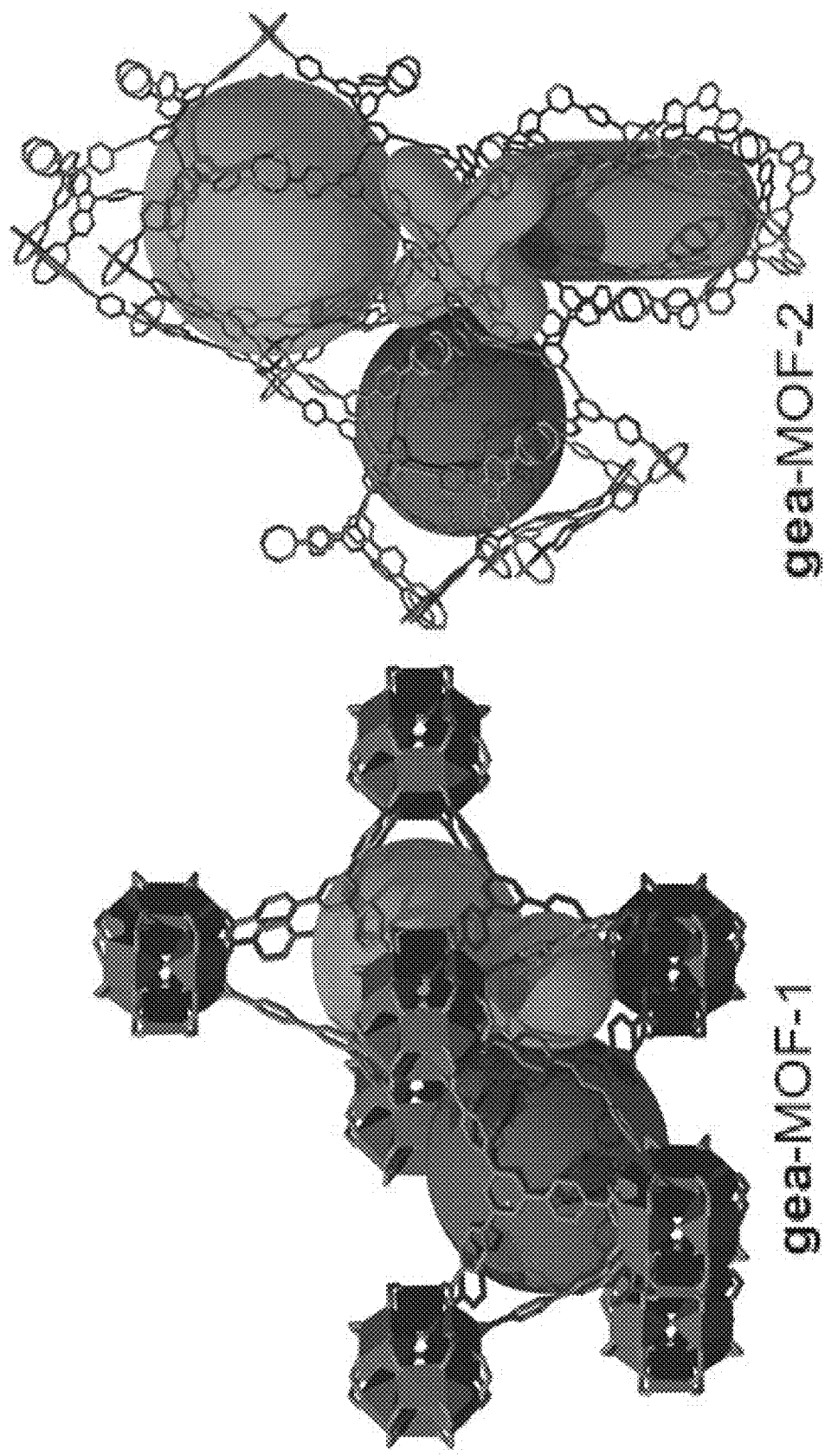
Figure 15B:
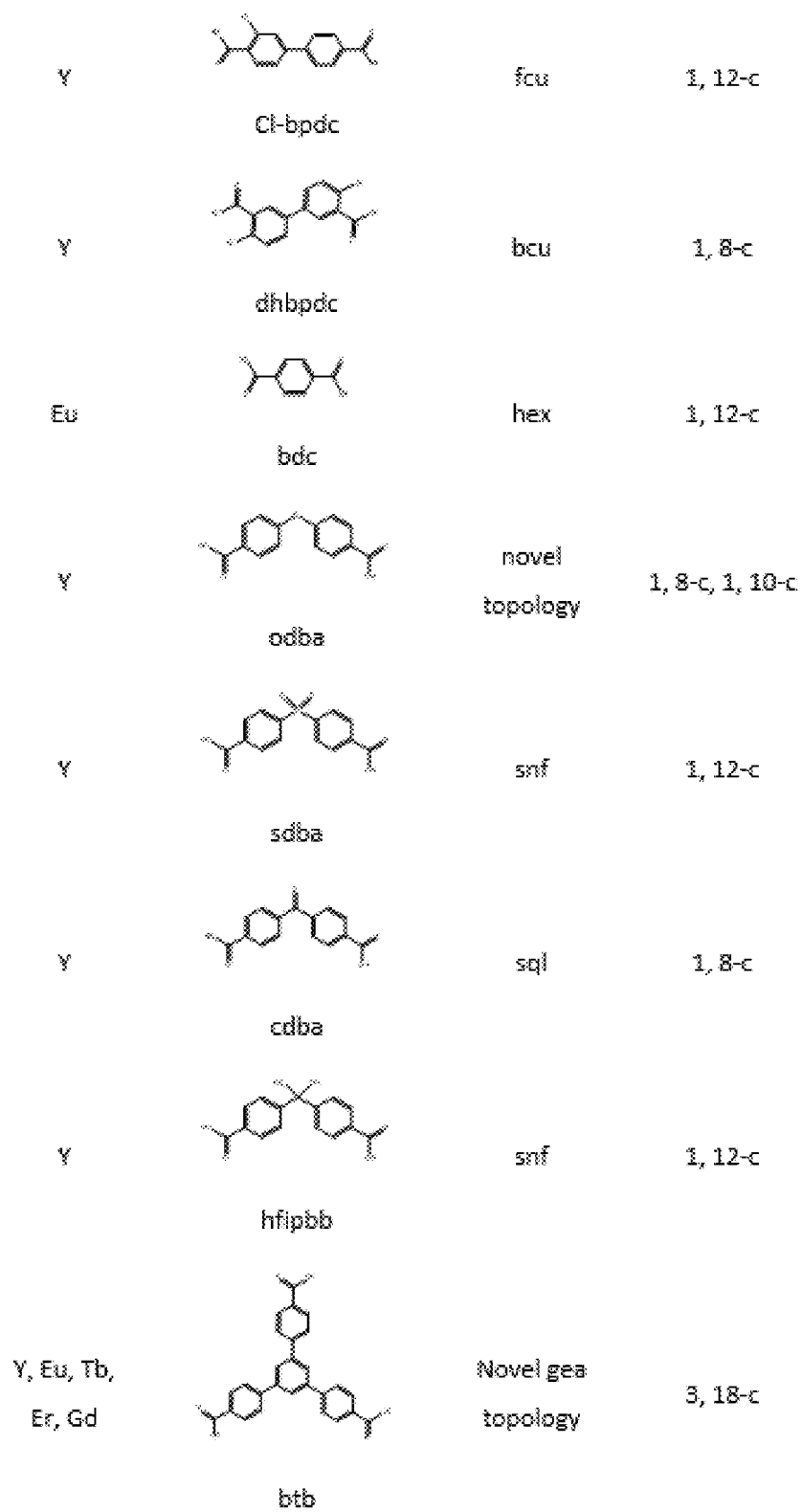
Figure 15C:
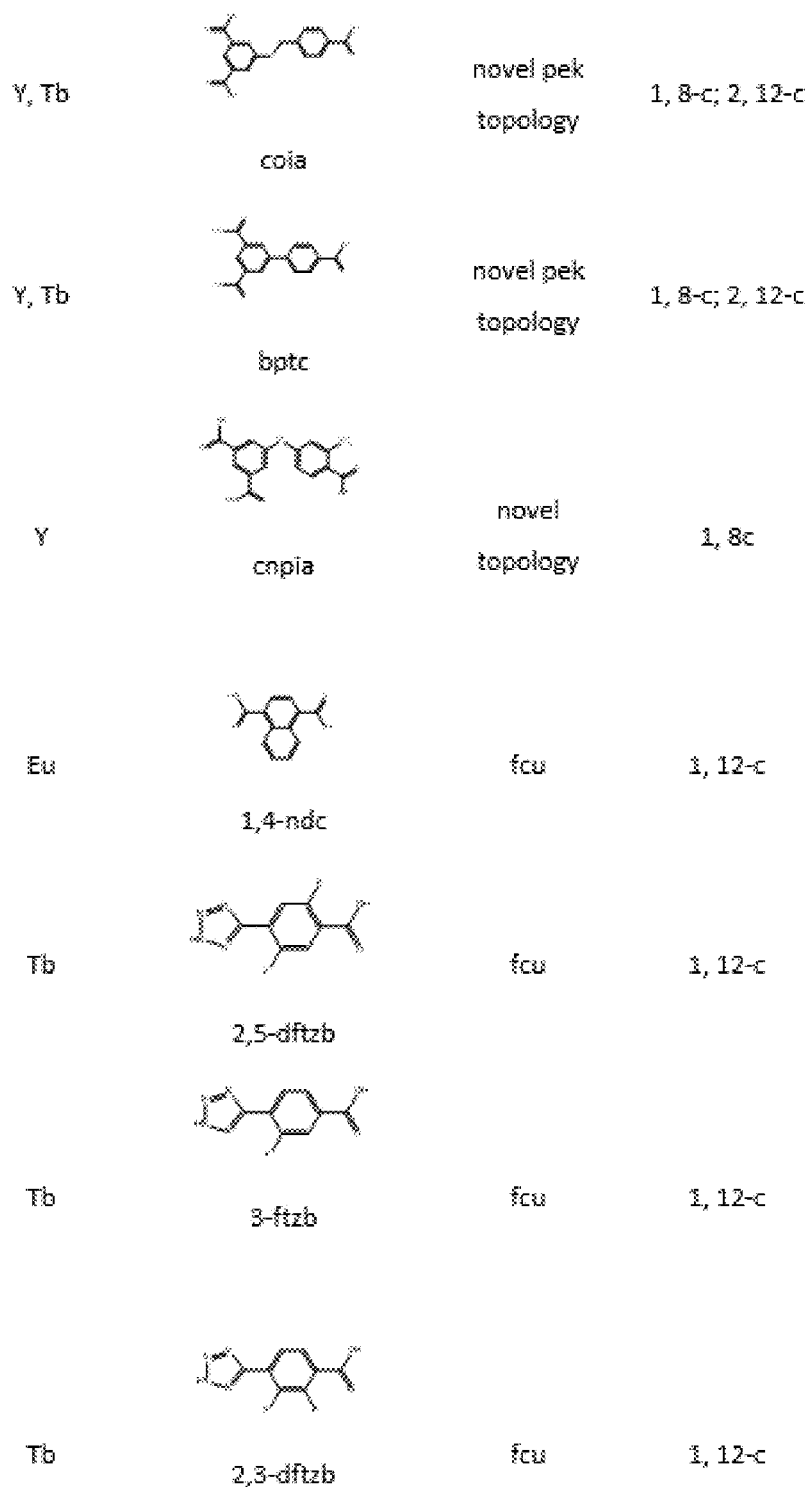
Figure 15D:
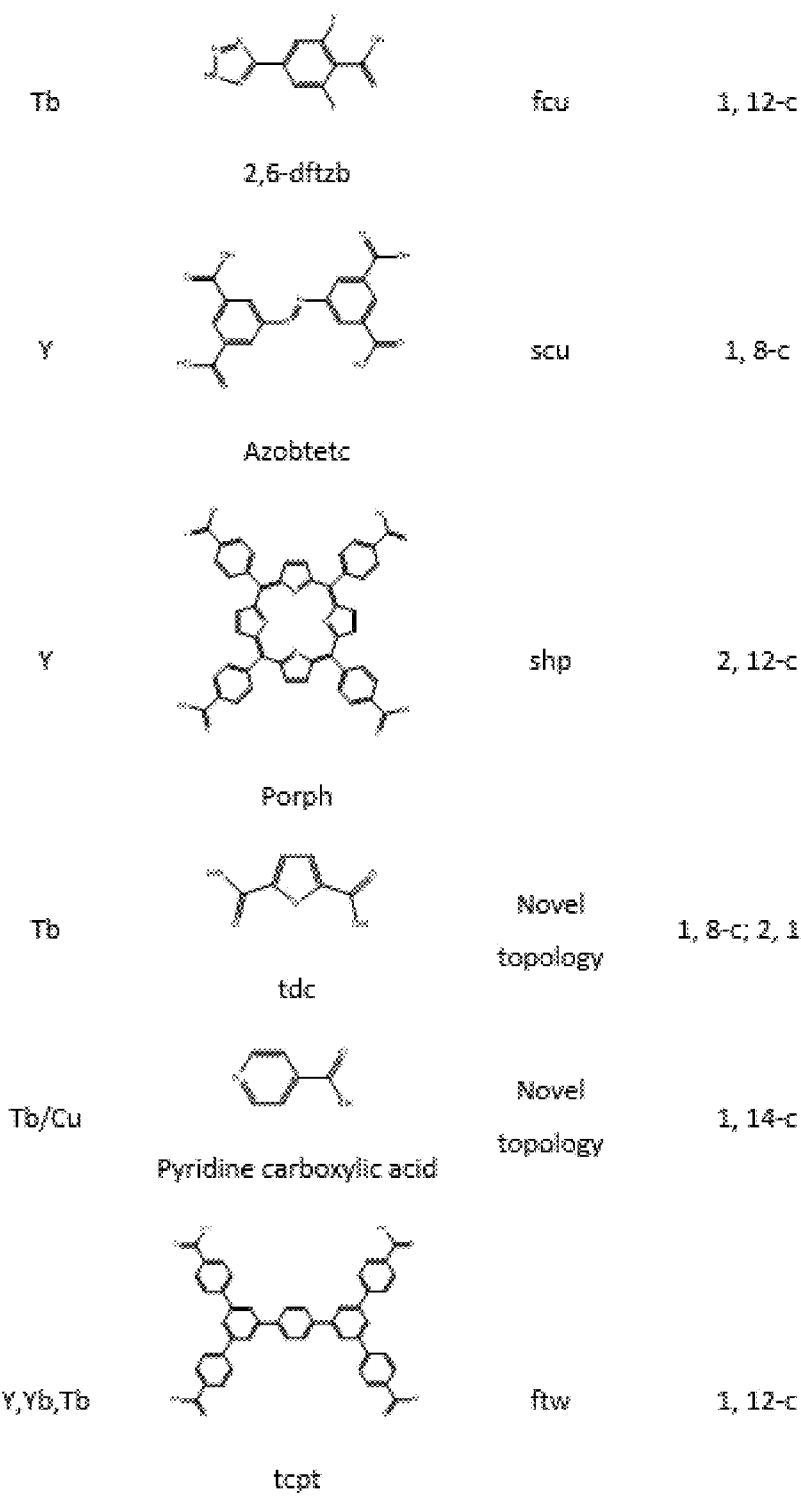
Figure 15E:
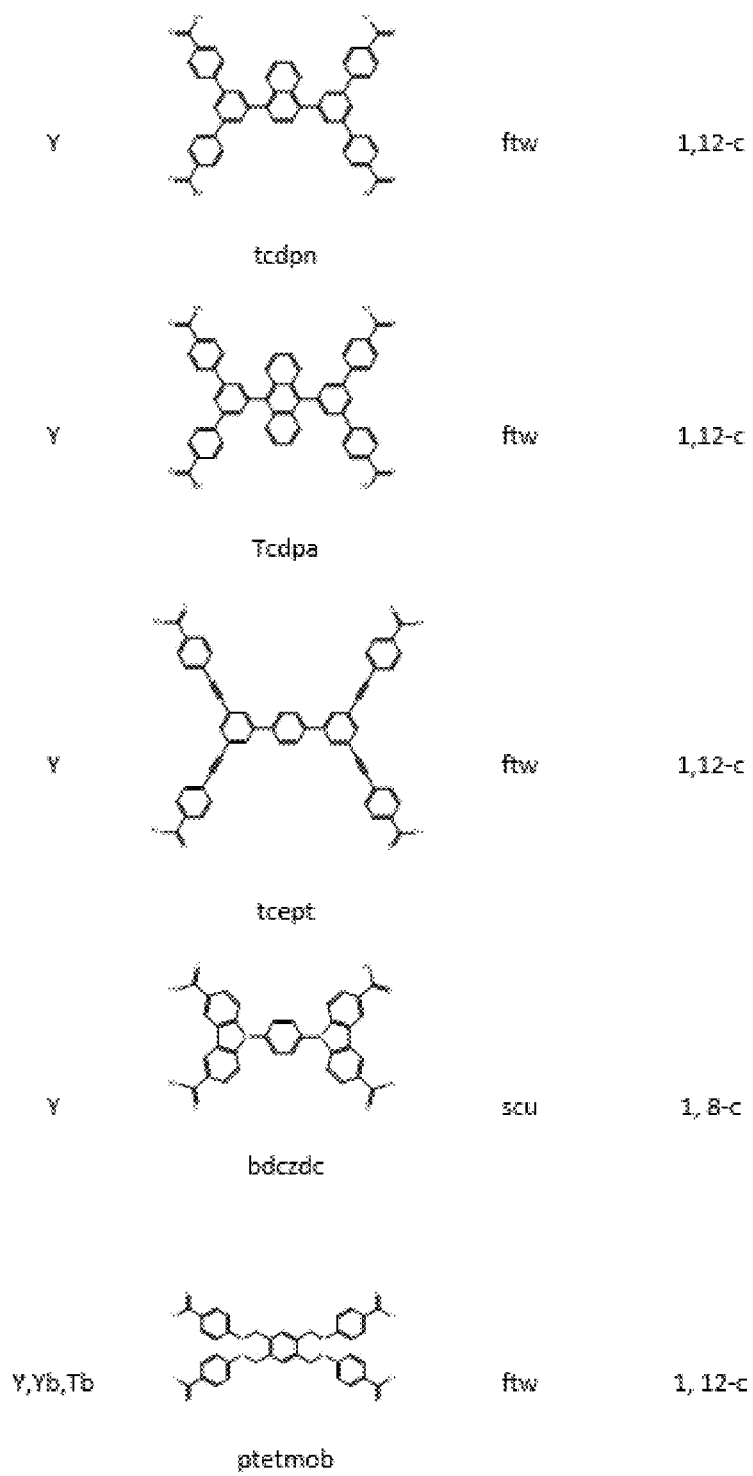

FIGS. 13A-B illustrate the structural differences between the gea-MOF-1 and gea-MOF-2 topologies. gea-MOF-2, formulated [(Cu$_3$(L)(H$_2$O)$_3$]n.(solv)x by SCD, crystallizes in a hexagonal system, the same as gea-MOF-1 but has a larger cell volume (88,962(5) Å3 versus 14,165.6(12) Å3), theoretical pore volume (2.76 cm3 g-1 versus 0.71 cm3 g-1), free volume (85.6% versus 61.7%) and much lower calculated density (0.29 g cm-3 versus 0.84 g cm-3). gea-MOF-1 exhibits three distinct cages (van der Waals (vdW) distances: cavity I, 22.4 Å×22.4 Å; cavity II, 24.8 Å×14.6 Å; cavity III, 11.2 Å×5.6 Å), cavity I being seen as a channel (aperture, vdW distances 12.8 Å×9.4 Å), and gea-MOF-2 exhibits a related pore system (vdW distances: cavity I, 41.7 Å×34.2 Å; cavity II, 44.5 Å×33.6 Å; cavity III, 21.2 Å×6.5 Å), but also contains an additional fourth cavity (cavity IV, eto [38.412], vdW distances 26.6 Å×15.6 Å) because of the substitution of the relatively dense inorganic cluster by an open MOP.

Further geometrical studies showed that the structure is expandable through five independent parameters, which allows a higher degree of tunability than that in rht-MOFs, for which only two independent expansion parameters have been reported thus far. From a purely topological point of view, this structure is an unprecedented and complex gwe topology: (3,3,3,4,4)-connected net, transitivity [5575]. Depending on the chosen simplification of the structure, gea-MOF-2 can be regarded in at least 5 other additional ways, leading each time to an unprecedented and complex topology: (3,3,3,3,3,3,3,3,3,3)-c net, corresponding to the augmented gwe-a topology; (4,4,4)-c net, geb topology; (6,6)-c net, gec topology; (3,5,5)-c net, ged topology, and (3,3,5,5)-c net, gea-a topology. Nevertheless, such a pentanodal net is far too convoluted and illustrates the difficulty in using the gwe net basic building units, namely squares and triangles, as a rational means to target MOFs based on this topology. It also shows the effectiveness of the SBB approach based on more elaborate building units (SBB, a MOP constructed from nine square copper paddlewheels [Cu$_2$(O$_2$CR)$_4$] bridged by 18 ligands) in embedding hierarchical information and thus coding for the rational design of a gea-related MOF, gea-MOF-2.

The SBB approach offers potential for systematically substituting dense clusters by relatively open MOPs to access additional functionalized spaces within more simple and already known nets (fcu, pcu, etc.) by careful choice of SBBs. In fact, as the complex pentanodal (five distinct vertices) gwe net is a descendent net of the gea net, it would have before been possible to design MOFs with gwe topology using the SBB approach, by first recognizing its relationship to the gea net and then employing geacoded building units (namely the 18-connected eto polyhedron and a triangle) if the gea and gwe nets were enumerated beforehand. Broadly, it is anticipated that certain complex polynodal nets can be partially deconstructed into their embedded polyhedra or layers; that is, keeping some of their basic building units grouped into elaborated building units coding for the net (net-coded building units). In this way, the SBB approach opens the door to a new and novel approach to designing solid-state materials by looking into extended solids from an alternative perspective.

Example 1: Cycloaddition of CO$_2$ and Propylene Oxide by gea-MOF-1

The high accessibility of the extended network of exposed metal centers and thermal stability of gea-MOF-1 structures make them highly suitable for heterogeneous catalysis. Thermal stability of porous catalytic structures is critical for efficiency in heterogeneous catalysis, such the cycloaddition of CO$_2$ and epoxides. Catalysis of cycloaddition of CO$_2$ and epoxides by gea-MOF-1 structures generally described by scheme 2:

Scheme S2. Synthesis of cyclic carbonates from CO$_2$ and epoxides catalysed by gea-MOF-1

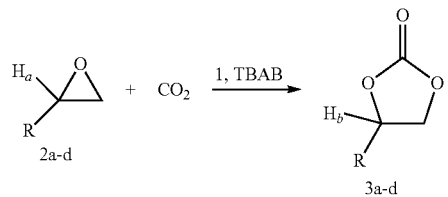

R = Me (2a), R = Et (2b)
R = Ph (2c), R = CH$_2$Cl (2d)

The results of this experiment can generally be used as a benchmark to test the suitability of gea-MOF-1, and others disclosed herein, for a variety of industrial applications including preparation of bulk chemicals. In particular, yttrium-based gea-MOF-1 structures are promising for a number of catalytic applications, including CO$_2$ conversion. In order to highlight the beneficial attributes of gea-MOF-1 structures, YCl$_3$ was first tested as a homogeneous catalyst for the cycloaddition of CO$_2$ and propylene oxide. YCl$_3$/TBAB (TBAB=tetrabutylammonium bromide) formed a powerful catalytic system for the conversion of CO$_2$, and high catalytic activity was observed under mild conditions of temperature and pressure (100° C., 10 bar). Under ambient conditions, the catalytic performance of YCl$_3$/TBAB was comparable to a known NbCl$_5$/TBAB catalyst (Table 1, Entries 1 and 2, respectively). Next, gea-MOF-1 was tested as heterogeneous catalyst under the same conditions as YCl$_3$/TBAB. Results are shown in Table 1:

TABLE 1

Catalytic activity of gea-MOF-1. Synthesis of cyclic carbonates from CO$_2$ and epoxides catalyzed by gea-MOF-1, referred in this catalysis section as compound 1.*

| Entry | R | Catalyst | Conv. (%) † | TON‡ | TOF (h$^{-1}$) § |
|---|---|---|---|---|---|
| 1♣ | Me | YCl$_3$, TBAB | 80 | 800 | 1067 |
| 2♥ | Me | YCl$_3$, TBAB | 75 | 75 | 19 |
| 3 | Me | TBAB | 16 | — | — |
| 4\| | Me | Y$_2$O$_3$, TBAB | 29 | 97 | 16 |
| 5 | Me | 1 | 6 | 40 | 7 |
| 6 | Me | 1, TBAB | 88 | 587 | 98 |
| 7¶ | Me | 1, TBAB | 86 | 573 | 96 |
| 8¶ | Me | 1, TBAB | 80 | 533 | 89 |
| 9¶ | Me | 1, TBAB | 77 | 513 | 86 |
| 10 | Et | 1, TBAB | 94 | 627 | 105 |

TABLE 1-continued

Catalytic activity of gea-MOF-1. Synthesis of cyclic carbonates from $CO_2$ and epoxides catalyzed by gea-MOF-1, referred in this catalysis section as compound 1.*

| Entry | R | Catalyst | Conv. (%) † | TON‡ | TOF ($h^{-1}$) § |
|---|---|---|---|---|---|
| 11 | Ph | 1, TBAB | 85 | 567 | 94 |
| 12 | $CH_2Cl$ | 1, TBAB | 89 | 593 | 99 |

*Unless otherwise noted all reaction were carried out by using epoxide 2a-d (100 mmol). 1 (60 mg, corresponding to 0.15 mmol of yttrium), TBAB (0.15 mmol) at 120° C., 20 bar for 6 h.
♣2a (100 mmol), $YCl_3$ (0.1 mmol), TBAB (0.1 mmol) at 100° C., 10 bar for 45 min.
♥2a (100 mmol), $YCl_3$ (1 mmol), TBAB (2 mmol) at 25° C., 1 bar $CO_2$ for 4 h.
†Conversion evaluated from the $^1H$ NMR spectrum by integration of epoxide vs. cyclic carbonate peaks.
‡ Turn over number (mmol of product/mmol of yttrium).
§ Turn over frequency
|2a (100 mmol), $Y_2O_3$ (0.15 mmol), TBAB (0.15 mmol).
¶With recycled catalyst 1 from previous entry.

As seen from Table 1, the tests on gea-MOF-1 proved that it can serve as an excellent recoverable catalyst for the solvent-free synthesis of carbonates 3a-3d under mild conditions in the presence of co-catalytic amounts of TBAB (Table 1, Entries 6-12). The gea-MOF-1 catalytic material was reused at least three times without showing any significant drop in catalytic performance (Table 1, Entries 6-9). Readily available $Y_2O_3$ was also tested as a heterogeneous catalyst for this reaction under similar conditions and as expected the catalytic results were significantly lower. The superior catalytic activity observed for gea-MOF-1 can be attributed to the higher accessibility of the Lewis acidic yttrium sites which is deemed necessary for epoxide activation as a first reaction step.

The catalyst, i.e. gea-MOF-1, was separated from the mixture at the end of the reaction via vacuum filtration. The solid was washed abundantly with dichloromethane (DCM) and MeOH, placed in a vial and soaked in MeOH for at least 6 h and subsequently dried under vacuum at room temperature. The quantity of catalyst recovered after each cycle was ca. 95% of the initial amount, and was still crystalline.

Example 2: Synthesis of Y-gea-MOF-1

Preparation of $(DMA^+)_2[Y_9(\mu_3\text{-}OH)_8(\mu_2\text{-}OH)_3((O_2C\text{—}C_6H_4)_3C_6H_3)_6]n.(solv.)x$, gea-MOF-1

A 15 solution of $Y(NO_3)_3 \cdot 6H_2O$ (8.6 mg, 0.0225 mmol), H3BTB (6.6 mg, 0.015 mmol), 2-FBA (95.2 mg, 0.675 mmol), DMF (2 mL) and $H_2O$ (0.5 mL) was prepared in a 20 mL scintillation vial and subsequently heated to 105° C. for 36 h in a preheated oven. The as-synthesized sample was purified through repeated washings with DMF to yield small colorless rod shaped crystals, which are insoluble in common organic solvents. Crystals were harvested, soaked in DMF overnight, and then exchanged in MeOH for one week. Note that MeOH was refreshed at least every 24 h. (Yield: 4 mg, 40% based on yttrium). Elemental Analysis: C=48.68% (theo: 49.38%), H=3.00% (3.19%), N=1.4% (0.48%). In the absence of 2-FBA, a previously reported MOF is isolated, i.e. Y-LOF (LOF: Lanthanide-Organic Framework). Same synthetic conditions can be applied using other rare earth nitrates (Eu, Tb, Er).

Example 3: Synthesis of Tb-pek-MOF

A solution of $Tb(NO3)_3 \cdot 5H_2O$ (29 mg, 0.068 mmol), H3L1 (3.4 mg, 0.012 mmol), 2-fluorobenzoic acid (285 mg, 2.04 mmol) in N,Ndimethylformamide (DMF) (3 mL), H2O (2 mL) and chlorobenzene (1 mL), was prepared in a 20 mL scintillation vial and subsequently heated to 105° C. for 72 h to give pure colorless hexagonal crystals. Crystals of 1 were harvested, washed with MeOH and air-dried. FT-IR (4000-650 cm-1): 3349 (br), 1611 (vs), 1574 (vs), 1438 (s), 1400 (vs), 1297 (w), 1252 (w), 1100 (w), 1018 (w), 871 (w), 776 (s), 761 (s), 713 (s). Elemental Analysis: C=28.2% (theo: 29.9%), H=3.0% (2.7%), N=2.3% (1.9%).

Example 4: Synthesis of Y-pek-MOF

A solution of $Y(NO_3)_3 \cdot 6H_2O$ (39 mg, 0.102 mmol), H3L1 (5 mg, 0.018 mmol), 2-fluorobenzoic acid (428 mg, 3.06 mmol) in DMF (4.5 mL), H2O (3 mL) and chlorobenzene (1.5 mL), was prepared in a 20 mL scintillation vial and subsequently heated to 105° C. for 72 h to give pure colorless hexagonal crystals. Crystals of 2 were harvested, washed with MeOH and air-dried. FT-IR (4000-650 cm-1): 2818 (br), 1612 (s), 1487 (w), 1465 (w), 1454 (w), 1407 (vs), 1305 (vs), 1225 (s), 1162 (w), 1135 (w), 1088 (w), 1033 (w), 918 (w), 869 (w), 844 (w), 793 (w), 751 (s), 714 (w), 687 (w). Elemental Analysis: C=35.1% (theo: 36.5%), H=3.5% (3.3%), N=2.2% (2.3%).

Example 5: Synthesis of Tb-pek-MOF

A solution of $Tb(NO_3)_3 \cdot 5H_2O$ (44 mg, 0.102 mmol), H3L2 (5.6 mg, 0.018 mmol), 2-fluorobenzoic acid (336 mg, 2.4 mmol) in DMF (4.5 mL), H2O (3 mL) and chlorobenzene (1.5 mL), was prepared in a 20 mL scintillation vial and subsequently heated to 105° C. for 72 h to give pure colorless hexagonal crystals. Crystals of 3 were harvested, washed with MeOH and air-dried. FT-IR (4000-650 cm-1): 3331 (br), 1593 (s), 1557 (s), 1449 (s), 1379 (vs), 1322 (s), 1265 (w), 1179 (w), 1129 (w), 1100 (w), 1036 (w), 1019 (w), 996 (w), 961 (w), 918 (w), 859 (w), 811 (w), 775 (s), 709 (s). Elemental Analysis: C=29.5% (theo: 29.9%), H=2.5% (2.8%), N=1.9% (1.8%).

Example 6: Synthesis of Y-pek-MOF

A solution of $Y(NO_3)_3 \cdot 6H_2O$ (26 mg, 0.068 mmol), H3L2 (2 mg, 0.006 mmol), 2-fluorobenzoic acid (224 mg, 1.6 mmol) in DMF (2.15 mL), H2O (2 mL) and chlorobenzene (1 mL), was prepared in a 20 mL scintillation vial and subsequently heated to 105° C. for 5 days to give pure colorless hexagonal crystals. Crystals of 4 were harvested, washed with MeOH and air-dried. FT-IR (4000-650 cm-1): 3422 (br), 2931 (w), 1621 (s), 1565 (s), 1496 (w), 1437 (w), 1407 (s), 1407 (s), 1386 (vs), 1320 (w), 1255 (s), 1178 (w), 1129 (w), 1096 (s), 1060 (w), 1020 (w), 995 (w), 962 (w), 890 (w), 865 (w), 812 (w), 780 (s), 709 (s). Elemental Analysis: C=32.2% (theo: 36.6%), H=3.4% (3.4%), N=2.3% (2.2%).

Example 7: Synthesis of Y-aea-MOF

A solution of $Y(NO_3)_3 \cdot 6H_2O$ (21.5 mg, 0.056 mmol), H3L3 (3.8 mg, 0.01 mmol), 2-fluorobenzoic acid (420 mg, 3 mmol) in DMF (4 mL), H2O (2 mL) and chlorobenzene (1 mL), was prepared in a 20 mL scintillation vial and subsequently heated to 105° C. for 2 days to give pure colorless hexagonal crystals. Crystals of 5 were harvested, washed with MeOH and air-dried. FT-IR (4000-650 cm-1): 1591 (s), 1545 (s), 1496 (w), 1398 (vs), 1277 (s), 779 (s), 709 (w). Elemental Analysis: C=36.4% (theo: 36.4%), H=2.4% (2.1%), N=1.9% (3.2%)

Example 8: Preparation of [(CuO₃)(L8)]ₙ·(solv)ₓ, gea-MOF-2
Synthesis of the hexacarboxylate ligand L8 (H6L).
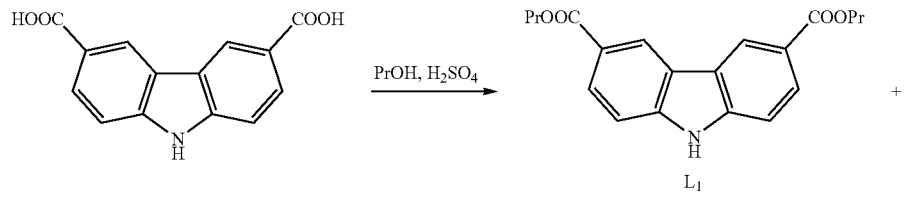
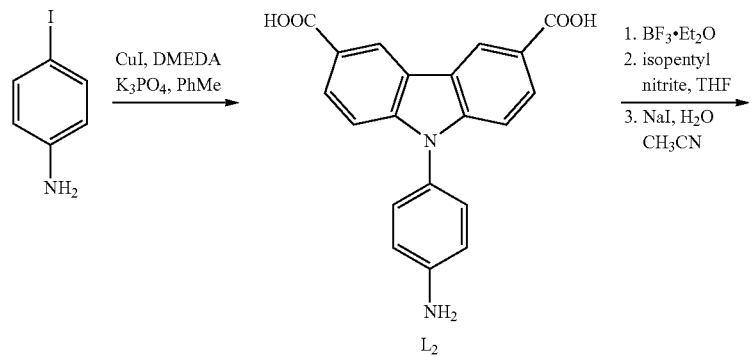
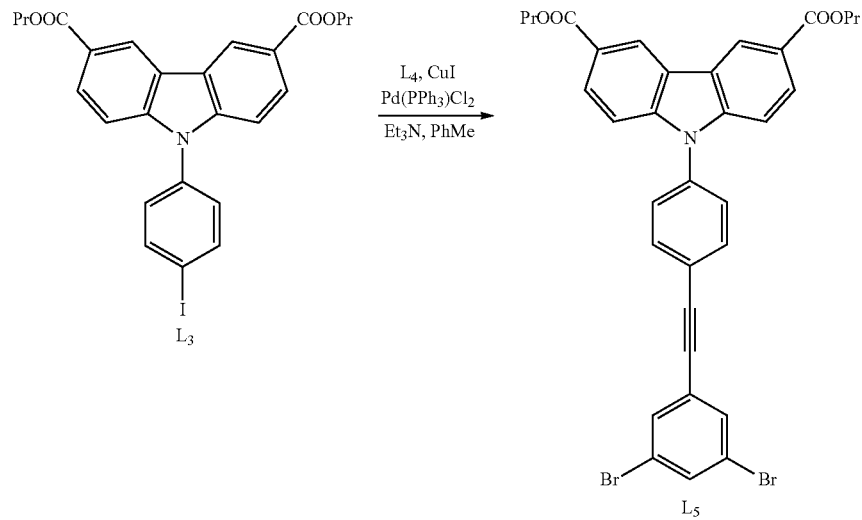
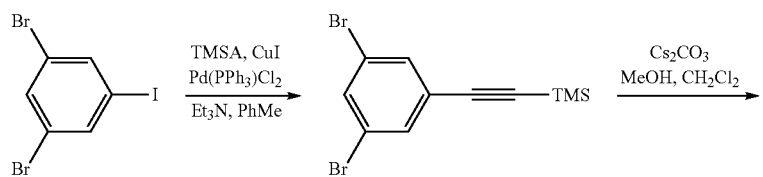

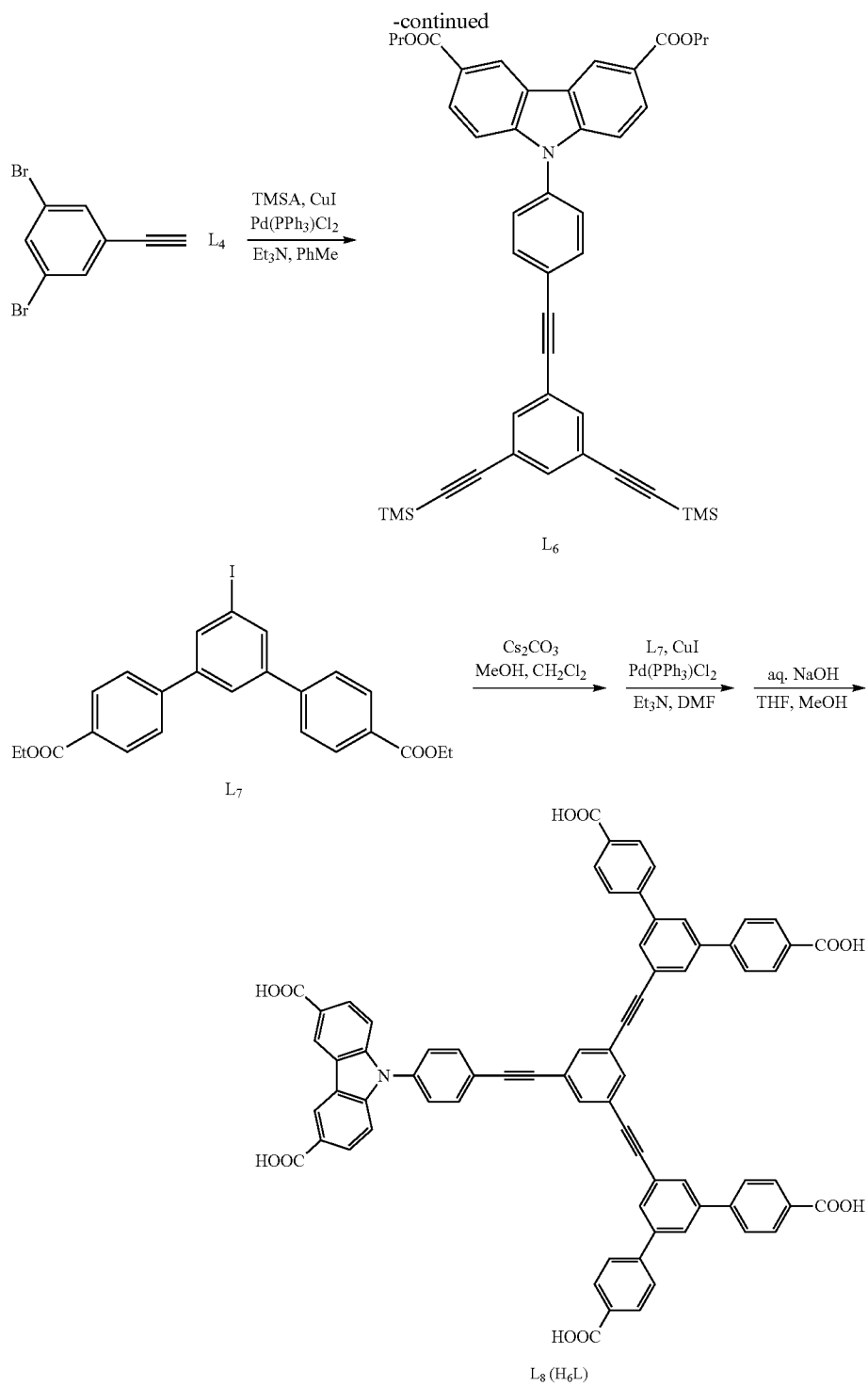

Preparation of dipropyl 9H-carbazole-3,6-dicarboxylate (L1)

9H-Carbazole-3,6-dicarboxylic acid (4.5 g, 17.6 mmol) was suspended in 1-propanol (110 mL), conc. $H_2SO_4$ (2 mL) was added and the mixture was stirred at 110° C. (oil bath) for 16 h. It was then cooled, concentrated on rotary evaporator and taken in $CH_2Cl_2$ (200 mL). The organic layer was subsequently washed with aq. $NaHCO_3$ (180 mL) and dried over $MgSO_4$. After filtration and removal of the solvent, cream solid was obtained in good purity (5.4 g, 90%). MW=339.

Preparation of Dipropyl 9-(4-aminophenyl)carbazole-3,6-dicarboxylate (L2)

Literature protocol was adapted: L (0.7 g, 2.1 mmol), 4-iodoaniline (0.45 g, 2.1 mmol), finely grounded $K_3PO_4$ (1.75 g, 8.3 mmol), CuI (59 mg, 0.3 mmol), N,N'-dimethylethylenediamine (DMEDA) (0.14 mL), dry toluene (15 mL) were added to a Schlenk flask under argon atmosphere and heated at 110° C. (oil bath) for 51 h. After cooling, the mixture was partitioned between 2/1/1 EtOAc/std. NH4Cl/water (120 mL), organic phase was separated, and then aqueous phase was further extracted with EtOAc (2×60 mL). Combined organics were dried over Na2SO4. After filtration and removal of the solvent, the residue was subjected to column chromatography (100% hexane to 50% AcOEt/hexane) to give off-white solid in sufficient purity (0.72 g, 81%). MW=430. Rf=0.2 (20% AcOEt/hexane).

Preparation of Dipropyl 9-(4-iodophenyl)carbazole-3,6-dicarboxylate (L3)

Literature protocol was adapted: $BF_3*Et_2O$ (0.8 mL, 6.3 mmol) was dissolved in dry THF (5 mL) and cooled to −20° C. (acetone bath) under nitrogen. A solution of L2 (0.7 g, 1.6 mmol) in dry THF (12 mL) was added dropwise for 5 minutes, followed by dropwise addition (10 min) of isopentyl nitrite (0.76 mL, 5.7 mmol) in dry THF (10 mL). Formation of the solid was observed. The mixture was stirred for 45 min at the same temperature, then allowed to warm to 0° C. over 30 min. Anhydrous $Et_2O$ (30 mL) was added dropwise, and the mixture was stirred at the same temperature for 5 minutes. The yellow solid (azonium BF4 salt) was filtered and dried briefly at suction (1 g). The crude salt was suspended in $CH_3CN$ (35 mL) and added to a solution of NaI (0.34 g, 2.3 mmol) in DI water (20 mL). After evolution of $N_2$ subsided, more DI water was added and the precipitate was filtered, washed with DI water, and dried at suction briefly. The compound was further dried at high vacuum at 40° C. overnight to yield cream solid in sufficient purity (0.67 g, 76%). MW=541. Rf=0.8 (20% AcOEt/hexane).

Preparation of 1,3-dibromo-5-ethynylbenzene (L4)

General Sonogashira coupling procedure: a mixture of dry toluene (20 mL)/triethylamine (5 mL) was degassed by bubbling argon through for 30 min. 1,3-Dibromo-5-iodobenzene (1 g, 2.76 mmol), bis(triphenylphosphine)-palladium(II) chloride (116 mg, 0.166 mmol), CuI (53 mg, 0.276 mmol), followed by trimethylsilylacetylene (TMSA, 0.47 mL, 3.31 mmol) were added, and the mixture was stirred at 45° C. for 16 h. After cooling, it was diluted with $CH_2Cl_2$ (60 mL), washed with water (50 mL), then 1N HCl (50 mL), and dried with $Na_2SO_4$. After filtration and removal of the solvent, the residue was chromatographed on silica using hexane as an eluent. Slightly yellow liquid was obtained (0.86 g, 94%). According to $^1H$ NMR, it contained up to 20% of 1-bromo-3,5-diethynylbenzene as an impurity.

The above mixture was dissolved in a mixture of MeOH (30 mL)/$CH_2Cl_2$ (15 mL) and $Cs_2CO_3$ (0.42 g, 1.3 mmol) was added, and then the mixture was stirred for 19 h at rt. 0.5 N HCl (40 mL)/$CH_2Cl_2$ (40 mL) was then added, phases separated, and then aqueous phase extracted again with $CH_2Cl_2$ (40 mL). Combined organics were dried with $Na_2SO_4$. After filtration and removal of the solvent, the residue was chromatographed on silica using hexane as an eluent. Less polar compound (first fraction) was separated to give white solid (0.5 g, 69% in 2 steps). MW=260.

Preparation of Dipropyl 9-{4-[(3,5-dibromophenyl)ethynyl]phenyl}-9H-carbazole-3,6-dicarboxylate (L5)

Using general Sonogashira coupling procedure as described for L4: to a degassed mixture of dry toluene (20 mL)/triethylamine (5 mL), L3 (0.6 g, 1.1 mmol), L4 (0.29 g, 1.1 mmol), bis(triphenylphosphine)palladium(II) chloride (47 mg, 0.067 mmol), and CuI (21 mg, 0.112 mmol) were added, and the mixture was stirred at 50° C. for 25 h. After cooling, it was diluted with $CH_2Cl_2$ (60 mL), washed with water containing little ammonia (50 mL), then 1N HCl (50 mL), and dried with $Na_2SO_4$. After filtration and removal of the solvent, the residue was chromatographed on silica using hexane to 70% $CH_2Cl_2$/hexane as an eluent. Light brown solid was obtained in sufficient purity (0.72 g, 96%). MW=673. Rf=0.5 (60% $CH_2Cl_2$/hexane).

Preparation of Dipropyl 9-{4-[(3,5-bis(trimethylsilylethynyl)phenyl)ethynyl]phenyl}-9H-carbazole-3,6-dicarboxylate (L6)

Using general Sonogashira coupling procedure as described for L4: to a degassed mixture of dry toluene (20 mL)/triethylamine (5 mL), L5 (0.7 g, 1.04 mmol), bis(triphenylphosphine)palladium(II) chloride (73 mg, 0.164 mmol), CuI (30 mg, 0.156 mmol) were added, followed by trimethylsilylacetylene (TMSA) (0.34 mL, 2.4 mmol) and the mixture was stirred at 40° C. for 25 h. After the same work-up as for L5, the residue was chromatographed on silica using hexane to 10% AcOEt/hexane as an eluent. Less polar compound (first fraction) was separated to give light yellow solid (0.505 g, 69%). MW=707.
Rf=0.5 (60% CH2Cl2/hexane).

Preparation of Ligand (L8, H6L)

L6 (0.49 g, 0.69 mmol) was dissolved in a mixture of MeOH/$CH_2Cl_2$ (1/1, 20 mL), $Cs_2CO_3$ (0.23 g, 0.69 mmol) was added, and then the mixture was stirred for 11 h at rt. 0.5 N HCl (40 mL)/$CH_2Cl_2$ (40 mL) was then added, phases separated, and then aqueous phase extracted again with $CH_2Cl_2$ (40 mL). Combined organics were dried with $Na_2SO_4$. After filtration and removal of the solvent, the residue was chromatographed on silica using hexane to AcOEt as an eluent, followed by $CH_2Cl_2$, to give 0.38 g of white solid. Rf=0.9 ($CH_2Cl_2$). According to $^1H$ NMR, a mixture of methyl/propyl esters in ca. 1/1 ratio was obtained.

The above mixture of esters (0.37 g) was reacted with diethyl 5'-iodo-1,1':3',1''-terphenyl-4,4''-dicarboxylate L7 (0.75 g, 1.5 mmol), bis(triphenylphosphine)palladium(II) chloride (58 mg, 0.082 mmol), CuI (26 mg, 0.137 mmol) in dry DMF (20 mL)/triethylamine (5 mL) at 50° C. for 36 h using general Sonogashira procedure as described for the synthesis of L4. After cooling, the mixture was diluted with water (150 mL), filtered, and solid washed thoroughly with ethyl acetate. The filter cake was dissolved in $CH_2Cl_2$ (200 mL), washed with water containing ammonia (100 mL), then brine (100 mL), and dried with $Na_2SO_4$. After filtration and removal of solvent, the hexaester was obtained as a yellow solid (0.716 g), which was taken into next step without further purification. Rf=0.5 (5% MeOH/$CH_2Cl_2$).

The hexaester (0.716 g) was suspended in THF (50 mL)/MeOH (15 mL), solution of NaOH (0.5 g, 12.5 mmol) in H2O (20 mL) was added, and the mixture was stirred at 90° C. for 12 h. After cooling, the mixture was concentrated on rotary evaporator, diluted with water to 100 mL vol., filtered through paper, and the filtrate was washed with AcOEt (50 mL). Then it was acidified with conc. HCl, and centrifuged (6000 rpm, 3 min). Centrifugation was repeated 3× with DI water to neutral pH, then with 1x acetone. Then the solid was suspended in acetone, concentrated on rotary evaporator and the residue was further dried under high vacuum at 40° C. overnight to yield brown solid in sufficient purity (0.47 g, 61% in 3 steps). MW=1111, C72H41NO12.

Preparation of [(CuO$_3$)(L8)]$_n$·(solv)$_x$, gea-MOF-2

A solution of Cu(BF$_4$)$_2$·2.5H$_2$O (1.8 mg, 0.0078 mmol), H$_6$L (1.6 mg, 0.0014 mmol), HNO$_3$ (3.5M, 0.1 mL), DMF (1.5 mL) and EtOH (0.5 mL) was prepared in a 20 mL scintillation vial and subsequently heated to 65° C. for 7 days in a preheated oven. The as-synthesized sample was purified through repeated washings with DMF to yield small blue hexagonal shaped crystals, which are insoluble in common organic solvents. Crystals were harvested, soaked in DMF overnight, and then exchanged in EtOH for one week. Note that EtOH was refreshed at least every 24 h.

FIGS. 14A-14C include a table showing examples of molecular building blocks (MBB), according to one or more embodiments of the present disclosure.

FIGS. 15A-15G include a table showing a list of examples of materials that have been synthesized and characterized, according to one or more embodiments of the present disclosure. The abbreviations for FIGS. 15A-15G were used: [a] Br-bdc=2-bromoterephthalic acid, NH2-bdc=2; aminoterephthalic acid; (NH2)$_2$-bdc=2,5-diaminoterephthalic acid; (OH)$_2$-bdc=2,5-dihydroxyterephthalic acid; NO2-bdc=2-nitroterephthalic acid; 2,6-ndc=2,6-naphthalene dicarboxylic acid; dhbpdc=4,4'-dihydroxybiphenyl-3,3'-dicarboxylic acid; bpdc=4,4'biphenyldicarboxylic acid; Cl-bpdc=3-chlorobiphenyl-4,4'-dicarboxylic acid; edba=ethine dibenzoic acid; bdc=1,4-benzene dicarboxylic acid; odba=oxybis(benzoic) acid; sdba=sulfonyl dibenzoic acid; cdba=benzophenone dicarboxylic acid; hfipbb=4,4'-(hexafluoroisopropylidene)bis(benzoic acid); btb=benzenetrisbenzoic acid; coia=5-((4-carboxybenzyl) oxy)isophthalic acid; bptc=[1,1'-biphenyl]-3,4',5-tricarboxylic acid; cnpia=5-(4-carboxy-3-nitrophenoxy)isophthalic acid; 1,4-ndc=naphthalene-1,4-dicarboxylic acid; 2,5-dftzb=2,5-difluoro-4-(2H-tetrazol-5-yl)benzoic acid; 3-ftzb=3-fluoro-4-(2H-tetrazol-5-yl)benzoic acid; 2,3-dftzb=2,3-difluoro-4-(2H-tetrazol-5-yl)benzoic acid; 2,6-dftzb=2,6-difluoro-4-(2H-tetrazol-5-yl)benzoic acid; Azobtetc=azobenzene tetracarboxylic acid; porph=porpyrintetracoarboxylic acid; tdc=thiophen dicarboxylic acid; tcpt=3,3",5,5"-tetrakis(4-carboxyphenyl)-p-terphenyl; tcdpn=3',3",5',5"-tetrakis(4-carboxyphenyl)-1,4-diphenylnaphthalene; tcdpa=3',3",5',5"-tetrakis(4-carboxyphenyl)-9,10-diphenylanthracene; tcept=3,3",5,5"-tetra-2-(4-carboxyphenyl)ethynyl-p-terphenyl; bdczdc=9,9'-(1,4-phenylene)bis(9H-carbazole-3,6-dicarboxylic acid); ptetmob=4,4',4",4'''-((benzene-1,2,4,5-tetrayltetrakis(methylene))tetrakis(oxy))tetrabenzoic acid; tdc=thiophene-2,5-dicarboxylic acid; adc=anthracene-9,10-dicarboxylic acid; 2,5-dfpbtz=5,5'-(2,5-difluoro-1,4-phenylene)bis(1H-tetrazole); 2,3-dfpbtz=5,5'-(2,3-difluoro-1,4-phenylene)bis(1H-tetrazole).

At least the following embodiments are described above.

Embodiment 1

Metal organic frameworks, comprising:
a plurality of polynuclear metal clusters; and
a plurality of polydentate ligands each linking to two or more of the metal clusters; wherein the polynuclear metal cluster includes at least seven metal ions.

2. The metal organic frameworks of embodiment 1, wherein the metal clusters comprise one or more lanthanide metals.

3. The metal organic frameworks of embodiment 1, wherein the metal clusters comprise one or more transition metals.

4. The metal organic frameworks of embodiment 1, wherein the metal clusters comprise one or more of Yttrium, Lanthanum, Cerium, Praseodymium, Neodymium, Samarium, Europium, Gadolinium, Terbium, Dysprosium, Holmium, Erbium, Thulium, Ytterbium and Lutetium.

5. The metal organic frameworks of embodiment 1, wherein the metal clusters comprise copper.

6. The metal organic frameworks of embodiment 1, wherein the clusters are in contact with a fluorinated group.

7. The metal organic frameworks of embodiment 1, wherein the ligands are tridentate.

8. The metal organic frameworks of embodiment 1, wherein at least one of the plurality of polydentate ligands comprise two or more coordinating groups which are the same.

9. The metal organic frameworks of embodiment 1, wherein at least one of the plurality of polydentate ligands comprise two or more coordinating groups which are different.

10 The metal organic frameworks of embodiment 1, wherein at least one of the coordinating groups in the plurality of ligands comprises a carboxylate, tetrazole, triazole, or sulfonate.

Embodiment 11

Metal organic frameworks, comprising:
a plurality of hexanuclear metal clusters; and
a plurality of tridentate ligands each linking to two or more of the metal clusters.

Embodiment 12

Metal organic frameworks, comprising:
a plurality of metal clusters, wherein each metal cluster is at least heptanuclear and in contact with a fluorinated group; and
a plurality of polydentate ligands linking to two or more metal clusters.

Embodiment 13

The metal organic frameworks of claim 12, wherein each of the metal clusters are at least nonanuclear.

Embodiment 14

A molecular building block composition, comprising:
a metal moiety including at least seven metal ions, and
a plurality of fluorinated precursor moieties.

15. The molecular building block of embodiment 14, wherein the metal moiety consists of nine metal ions.

16. The molecular building block of embodiment 14, wherein the metal clusters comprise one or more lanthanide metals.

17. The molecular building block of embodiment 14, wherein the metal clusters comprise one or more transition metals 18. The molecular building block of embodiment 14, wherein the metal clusters comprise one or more of Yttrium, Lanthanum, Cerium, Praseodymium, Neodymium, Samarium, Europium, Gadolinium, Terbium, Dysprosium, Holmium, Erbium, Thulium, Ytterbium and Lutetium.

19. The molecular building block of embodiment 14, further comprising a solvent associated with the precursor moiety.

20. The molecular building block of embodiment 19, wherein the solvent comprises one or more of H₂O, Dimethylformamide (DMF), dimethylamine (DMA), dimethyl ammonium or formate.

Embodiment 21

Metal organic frameworks, comprising:
a plurality of polynuclear metal clusters; and
a plurality of polydentate ligands each linking to two or more of the metal clusters;
wherein the polynuclear metal cluster includes at least one rare earth metal and has a ftw topology.

Embodiment 22

A metal organic framework composition comprising a gea topology.
23. The metal organic framework composition of embodiment 22, wherein the gea topology comprises gea-MOF-1 topology.
24. The metal organic framework composition of embodiment 22, wherein the gea topology comprises gea-MOF-2 topology.
25. The metal organic framework composition of embodiment 23, wherein the gea topology comprises a transposition of a gea-MOF lanthanide based MBB to a gea-MOF metal based MOP.

Embodiment 26

Metal organic frameworks, comprising:
a plurality of polynuclear metal clusters; and
a plurality of polydentate ligands each linking to two or more of the metal clusters;
wherein the polynuclear metal cluster includes at least one rare earth metal and has a pek topology.

Embodiment 27

Metal organic frameworks, comprising:
a plurality of polynuclear metal clusters; and
a plurality of polydentate ligands each linking to two or more of the metal clusters;
wherein the polynuclear metal cluster includes at least one rare earth metal and has a aea topology.

Embodiment 28

A method for making a metal organic framework, the method comprising:
contacting a metal ion component, a fluorinated precursor, and a polydentate ligand to form a mixture;
allowing the mixture to react such that a crystalline metal organic framework can form.

A number of embodiments of the invention have been described. Nevertheless, it will be understood that various modifications may be made without departing from the spirit and scope of the invention. Accordingly, other embodiments are within the scope of the following claims:

What is claimed is:
1. A molecular building block composition comprising:
a metal moiety comprising nine metal ions, wherein the metal moiety has 12, 14, or 18 points of extension, and
a plurality of fluorinated precursor moieties.

2. The molecular building block composition of claim 1, wherein the metal moiety is a nonanuclear metal cluster coordinated by at least one polytopic ligand.
3. The molecular building block composition of claim 2, wherein the at least one polytopic ligand is selected from the group consisting of 1,3,5-benzene(tris)benzoate, biphenyl-3,4,5-tricarboxylic acid, 5-(4-carboxybenzyloxy)-isophthalic acid, 4,4'-(pyridine-2,6-diyl)dibenzoic acid, carbazole-3,6-dicarboxylic acid, 5',5''''-((5-((4-(3,6-dicarboxy-9H-carbazol-9-yl)phenyl)ethynyl)-1,3-phenylene)bis(ethyne-2,1-iyl))bis([1,1':3',1''-terphenyl]-4,4''-dicarboxylic acid), 9-(4-carboxyphenyl)-9Hcarbazole-3,6-dicarboxylic acid, 2-bromoterephthalic acid, aminoterephthalic acid, 2,5-diaminoterephthalic acid, 2,5-dihydroxyterephthalic acid, 2-nitroterephthalic acid, 2,6-naphthalene dicarboxylic acid, 4,4'-dihydroxybiphenyl-3,3'-dicarboxylic acid, 4,4'-biphenyldicarboxylic acid, 3-chlorobiphenyl-4,4'-dicarboxylic acid, ethine dibenzoic acid, 1,4-benzene dicarboxylic acid, oxybis(benzoic) acid, sulfonyl dibenzoic acid, benzophenone dicarboxylic acid, 4,4'-(hexafluoroisopropylidene)bis(benzoic acid), 5-((4-carboxybenzyl)oxy)isophthalic acid, [1,1'-biphenyl]-3,4',5-tricarboxylic acid, 5-(4-carboxy-3-nitrophenoxy)isophthalic acid, naphthalene-1,4-dicarboxylic acid, 2,5-difluoro-4-(2H-tetrazol-5-yl)benzoic acid, 3-fluoro-4-(2H-tetrazol-5-yl)benzoic acid, 2,3-difluoro-4-(2H-tetrazol-5-yl)benzoic acid, 2,6-difluoro-4-(2H-tetrazol-5-yl)benzoic acid, azobenzene tetracarboxylic acid, porpyrintetracoarboxylic acid, thiophen dicarboxylic acid, 3,3'',5,5''-tetrakis(4-carboxyphenyl)-p-terphenyl, 3',3'',5',5''-tetrakis(4-carboxyphenyl)-1,4-diphenylnaphthalene, 3',3'',5',5''-tetrakis(4-carboxyphenyl)-9,10-diphenylanthracene, 3,3'',5,5''-tetra-2-(4-carboxyphenyl)ethynyl-p-terphenyl, 9,9'-(1,4-phenylene)bis(9H-carbazole-3,6-dicarboxylic acid), 4,4',4'',4'''-((benzene-1,2,4,5-tetrayltetrakis(methylene))tetrakis(oxy))tetrabenzoic acid, thiophene-2,5-dicarboxylic acid, anthracene-9,10-dicarboxylic acid, 5,5'-(2,5-difluoro-1,4-phenylene)bis(1H-tetrazole), and 5,5'-(2,3-difluoro-1,4-phenylene)bis(1H-tetrazole).
4. The molecular building block composition of claim 1, wherein the metal moiety comprises at least two polytopic ligands.
5. The molecular building block composition of claim 4, wherein the at least two polytopic ligands are independently selected from the group consisting of 1,3,5-benzene(tris)benzoate, biphenyl-3,4,5-tricarboxylic acid, 4,4'-(pyridine-2,6-diyl)dibenzoic acid, carbazole-3,6-dicarboxylic acid, 5',5''''-((5-((4-(3,6-dicarboxy-9H-carbazol-9-yl)phenyl)ethynyl)-1,3-phenylene)bis(ethyne-2,1-diyl))bis([1,1':3',1''-terphenyl]-4,4''-dicarboxylic acid), 9-(4-carboxyphenyl)-9Hcarbazole-3,6-dicarboxylic acid, 2-bromoterephthalic acid, aminoterephthalic acid, 2,5-diaminoterephthalic acid, 2,5-dihydroxyterephthalic acid, 2-nitroterephthalic acid, 2,6-naphthalene dicarboxylic acid, 4,4'-dihydroxybiphenyl-3,3'-dicarboxylic acid, 4,4'-biphenyldicarboxylic acid, 3-chlorobiphenyl-4,4'-dicarboxylic acid, ethine dibenzoic acid, 1,4-benzene dicarboxylic acid, oxybis(benzoic) acid, sulfonyl dibenzoic acid, benzophenone dicarboxylic acid, 4,4'-(hexafluoroisopropylidene)bis(benzoic acid), 5-((4-carboxybenzyl)oxy)isophthalic acid, [1,1'-biphenyl]-3,4',5-tricarboxylic acid, 5-(4-carboxy-3-nitrophenoxy)isophthalic acid, naphthalene-1,4-dicarboxylic acid, 2,5-difluoro-4-(2H-tetrazol-5-yl)benzoic acid, 3-fluoro-4-(2H-tetrazol-5-yl)benzoic acid, 2,3-difluoro-4-(2H-tetrazol-5-yl)benzoic acid, 2,6-difluoro-4-(2H-tetrazol-5-yl)benzoic acid, azobenzene tetracarboxylic acid, porpyrintetracoarboxylic acid, thiophen dicarboxylic acid, 3,3'',5,5''-tetrakis(4-carboxyphenyl)-p-terphenyl, 3',3'',5',5''-tetrakis(4-carboxyphenyl)-

1,4-diphenylnaphthalene, 3',3''',5',5'''-tetrakis(4-carboxyphenyl)-9,10-diphenylanthracene, 3,3''',5,5'''-tetra-2-(4-carboxyphenyl)ethynyl-p-terphenyl, 9,9'-(1,4-phenylene)bis(9H-carbazole-3,6-dicarboxylic acid), 4,4',4'',4'''-((benzene-1,2,4,5-tetrayltetrakis(methylene))tetrakis(oxy)) tetrabenzoic acid, thiophene-2,5-dicarboxylic acid, anthracene-9,10-dicarboxylic acid, 5,5'-(2,5-difluoro-1,4-phenylene)bis(1H-tetrazole), and 5,5'-(2,3-difluoro-1,4-phenylene)bis (1H-tetrazole).

6. The molecular building block composition of claim 1, wherein the metal ions comprise one or more lanthanide metal ions.

7. The molecular building block composition of claim 1, wherein the metal ions comprise one or more transition metal ions.

8. The molecular building block composition of claim 1, wherein the metal ions comprise one or more rare earth metal ions.

9. The molecular building block composition of claim 1, wherein the metal moiety comprises one or more metals selected from the group consisting of Yttrium, Lanthanum, Cerium, Praseodymium, Neodymium, Samarium, Europium, Gadolinium, Terbium, Dysprosium, Holmium, Erbium, Thulium, Ytterbium and Lutetium.

10. The molecular building block composition of claim 1, further comprising a solvent associated with at least one of the fluorinated precursor moieties.

11. The molecular building block composition of claim 10, wherein the solvent is selected from the group consisting of $H_2O$, dimethylformamide (DMF), dimethylamine (DMA), dimethyl ammonium, and formate, or a combination thereof.

12. The molecular building block composition of claim 1, wherein at least one of the fluorinated precursor moieties is selected from the group consisting of fluorine containing ligands and 2-fluorobenzoic acid.

13. The molecular building block composition of claim 12, wherein the composition comprises 2-fluorobenzoic acid and the metal moiety is represented by the formula $RE_9(\mu_3\text{-}OH)_8(\mu_2\text{-}OH)_3(O_2C\text{---})_{18}$, wherein RE is a rare earth metal ion selected from the group consisting of Yttrium, Terbium, Erbium, and Europium, or a combination thereof, and wherein $\mu_3$-OH and $\mu_2$-OH are hydroxyl-functionalized bridging ligands and $O_2C$— is a terminal ligand.

14. A secondary building unit composition comprising at least two connected molecular building blocks, wherein at least one molecular building block comprises:
 a metal moiety comprising nine metal ions, and
 a plurality of fluorinated precursor moieties,
wherein the metal moiety is a nonanuclear metal cluster coordinated by at least one polytopic ligand, wherein the at least one polytopic linker is selected from the group consisting of 1,3,5-benzene(tris)benzoate, biphenyl-3,4,5 tricarboxylic acid, 5-(4-carboxybenzyloxy)-isophthalic acid, 4,4'-(pyridine-2,6-diyl)dibenzoic acid, carbazole-3,6-dicarboxylic acid, 5',5''''-((5-((4-(3,6-dicarboxy-9H-carbazol-9-yl)phenyl)ethynyl)-1,3-phenylene)bis(ethyne-2,1-diyl))bis([1,1':3',1''-terphenyl]-4,4'' dicarboxylic acid), 9-(4-carboxyphenyl)-9Hcarbazole-3,6-dicarboxylic acid, 2 bromoterephthalic acid, aminoterephthalic acid, 2,5-diaminoterephthalic acid, 2,5-dihydroxyterephthalic acid, 2-nitroterephthalic acid, 2,6-naphthalene dicarboxylic acid, 4,4'-dihydroxybiphenyl-3,3'-dicarboxylic acid, 4,4'-biphenyldicarboxylic acid, 3-chlorobiphenyl-4,4'-dicarboxylic acid, ethine dibenzoic acid, 1,4-benzene dicarboxylic acid, oxybis(benzoic) acid, sulfonyl dibenzoic acid, benzophenone dicarboxylic acid, 4,4' (hexafluoroisopropylidene)bis(benzoic acid), 5-((4-carboxybenzyl)oxy) isophthalic acid, [1,1'-biphenyl]-3,4',5-tricarboxylic acid, 5-(4-carboxy-3-nitrophenoxy)isophthalic acid, naphthalene-1,4-dicarboxylic acid, 2,5-difluoro-4-(2H-tetrazol-5-yl)benzoic acid, 3-fluoro-4-(2H-tetrazol-5-yl)benzoic acid, 2,3-difluoro-4-(2H-tetrazol-5-yl)benzoic acid, 2,6-difluoro-4-(2H-tetrazol-5-yl)benzoic acid, azobenzene tetracarboxylic acid, porpyrintetracoarboxylic acid, thiophen dicarboxylic acid, 3,3''',5,5'''-tetrakis(4-carboxyphenyl)-p-terphenyl, 3',3''',5',5'''-tetrakis(4-carboxyphenyl)-1,4-diphenylnaphthalene, 3',3''',5',5'''-tetrakis(4-carboxyphenyl)-9,10-diphenylanthracene, 3,3''',5,5'''-tetra-2-(4-carboxyphenyl)ethynyl-p-terphenyl, 9,9'-(1,4-phenylene)bis(9H-carbazole-3,6-dicarboxylic acid), 4,4',4'',4'''-((benzene-1,2,4,5-tetrayltetrakis(methylene))tetrakis(oxy))tetrabenzoic acid, thiophene-2,5-dicarboxylic acid, anthracene-9,10-dicarboxylic acid, 5,5'-(2,5-difluoro-1,4-phenylene)bis(1H-tetrazole), and 5,5'-(2,3-difluoro-1,4-phenylene)bis(1H-tetrazole).

15. The secondary building unit composition of claim 14, further comprising a hexanuclear metal cluster.

16. The secondary building unit composition of claim 15, wherein the hexanuclear metal cluster comprises a metal selected from the group consisting of Yttrium, Lanthanum, Cerium, Praseodymium, Neodymium, Samarium, Europium, Gadolinium, Terbium, Dysprosium, Holmium, Erbium Thulium, Ytterbium, and Lutetium, or a combination thereof.

17. The secondary building unit composition of claim 14, wherein at least one molecular building block comprises nine copper paddlewheels bridged by 18 hexacarboxylate ligands.

\* \* \* \* \*